US009653785B2

(12) United States Patent
Vance

(10) Patent No.: US 9,653,785 B2
(45) Date of Patent: May 16, 2017

(54) ANTENNAS FOR BODY-WORN WIRELESS ELECTRONIC DEVICES

(71) Applicant: Sony Corporation, Tokyo (JP)

(72) Inventor: Scott L. Vance, Staffanstorp (SE)

(73) Assignees: Sony Corporation, Tokyo (JP); Sony Mobile Communications Inc., Tokyo (JP)

( * ) Notice: Subject to any disclaimer, the term of this patent is extended or adjusted under 35 U.S.C. 154(b) by 23 days.

(21) Appl. No.: 14/603,438

(22) Filed: Jan. 23, 2015

(65) Prior Publication Data

US 2016/0218419 A1 Jul. 28, 2016

(51) Int. Cl.
| | |
|---|---|
| *H01Q 1/12* | (2006.01) |
| *H01Q 1/27* | (2006.01) |
| *H01Q 1/24* | (2006.01) |
| *A61B 5/00* | (2006.01) |
| *A61B 5/024* | (2006.01) |
| *A61B 5/08* | (2006.01) |
| *A61B 5/11* | (2006.01) |

(52) U.S. Cl.
CPC .......... *H01Q 1/273* (2013.01); *A61B 5/0015* (2013.01); *A61B 5/681* (2013.01); *H01Q 1/241* (2013.01); *A61B 5/02438* (2013.01); *A61B 5/0816* (2013.01); *A61B 5/11* (2013.01)

(58) Field of Classification Search
CPC ....... H01Q 1/273; H01Q 1/241; A61B 5/0015
See application file for complete search history.

(56) References Cited

U.S. PATENT DOCUMENTS

| | | | |
|---|---|---|---|
| 6,047,163 A | 4/2000 | Miyoshi | |
| 8,121,662 B2 | 2/2012 | Martin et al. | |
| 8,350,695 B2 | 1/2013 | Loen | |
| 8,570,838 B2* | 10/2013 | Fujisawa | G04C 10/02 343/718 |
| 8,787,006 B2 | 7/2014 | Golko et al. | |
| 8,913,466 B2* | 12/2014 | Fujisawa | G04R 60/12 343/718 |
| 2007/0146218 A1* | 6/2007 | Turner | H01Q 1/273 343/718 |
| 2009/0033565 A1* | 2/2009 | Yen | H01Q 1/242 343/702 |

(Continued)

FOREIGN PATENT DOCUMENTS

EP 1 615 187 A1 1/2006

OTHER PUBLICATIONS

Shrestha, Sudhir, et al., Flexible Microstrip Antenna for Skin Contact Application, *International Journal of Antennas and Propogation*, vol. 2012, Article ID 745426, 5 pages No. 2.

(Continued)

*Primary Examiner* — Trinh Dinh
(74) *Attorney, Agent, or Firm* — Myers Bigel, P.A.

(57) ABSTRACT

A wearable wireless electronic device to be worn on a wrist of a user includes a first conductive antenna element of an antenna that is electrically coupled to an antenna feed of the antenna and a second conductive antenna element of the antenna that is electrically coupled to a ground plane of the antenna. The first conductive antenna element and the second conductive antenna element are configured to be in contact with and/or in close proximity to a wrist of the user that is wearing the wearable first wireless electronic device.

27 Claims, 21 Drawing Sheets

(56) References Cited

U.S. PATENT DOCUMENTS

| | | | |
|---|---|---|---|
| 2009/0284433 A1* | 11/2009 | Tsutsumi | ............... H01Q 1/243 |
| | | | 343/825 |
| 2013/0214979 A1 | 8/2013 | McMilin et al. | |
| 2014/0055309 A1 | 2/2014 | Jenwatanavet | |
| 2014/0253394 A1 | 9/2014 | Nissinen et al. | |

OTHER PUBLICATIONS

International Search Report and Written Opinion Corresponding to International Application No. PCT/JP2015/003696; Date of Mailing: Oct. 29, 2015; 12 Pages.

\* cited by examiner

ANTENNAS FOR BODY-WORN WIRELESS ELECTRONIC DEVICES

TECHNICAL FIELD

The present inventive concepts generally relate to the field of wireless communications and, more specifically, to antennas for wireless communication devices.

BACKGROUND

Wearable wireless communication devices such as cell phones, medical monitoring equipment, and other user equipment may be worn on or be in close proximity to a part of the user's body such as a wrist. The antennas of these body worn devices may experience performance degradation when in contact with or in close proximity to the body. Some antenna designs, when part of a body-worn device, may result in an undesirable amount of absorption, body loss and/or return loss of electromagnetic communication signals.

SUMMARY

Various embodiments of the present inventive concepts include a wearable wireless electronic device to be worn on a wrist of a user. The wearable wireless electronic device may include a first conductive antenna element of an antenna that is electrically coupled to an antenna feed of the antenna and a second conductive antenna element of the antenna that is electrically coupled to the ground plane of the antenna. The first conductive antenna element and the second conductive antenna element may be configured to be in contact with and/or in close proximity to a wrist of the user that is wearing the wearable first wireless electronic device.

According to various embodiments, the first and second conductive antenna elements may be configured to provide coupling between the wrist of the user and the antenna such that the antenna resonates at one or more resonant frequencies when coupled to the wrist of the user. The coupling between the wrist of the user and the antenna may provide impedance matching to the antenna to reduce return loss of the antenna when coupled to the wrist of the user. The first and second conductive antenna elements may be configured to reduce the impedance matching of the antenna when the wearable wireless electronic device is removed from contact with and/or the close proximity to the wrist of the user. The first and second conductive antenna elements may be configured to prevent the antenna from resonating at the one or more resonant frequencies when the wearable wireless electronic device is removed from contact with and/or from the close proximity to the wrist of the user.

In some embodiments, the one or more resonant frequencies may include a lowband resonant frequency and a highband resonant frequency that is higher than the lowband resonant frequency. The lowband resonant frequency may include frequencies between about 700 MHz and 1000 MHz. The highband resonant frequency may include frequencies between 1.5 GHz and 2.5 GHz.

According to various embodiments, the wearable wireless electronic device may include a case with a first face and a second face that is remote the first face. The second face may be adjacent the wrist of the user. There may be a plurality of microelectronic devices in the case. The first and second conductive antenna elements may be outside the case, protruding from the second face of the case toward the wrist of the user.

In some embodiments, the second conductive antenna element may extend from a coupling via along the second face of the case, away from an edge of the case. The coupling via may be located near the edge of the case and may electrically couple the second conductive antenna element to the ground plane of the antenna. The second conductive antenna element may include a fork-shaped structure that extends along the second face of the case. The second conductive antenna element may include one or more hollow half moon-shaped structures that extend along the second face of the case. The second conductive antenna element may include one or more filled half moon-shaped structures that extend along the second face of the case. The first conductive antenna element may include at least one approximately circular shape along an edge of the case that extends along the second face of the case. The at least one approximately circular shape may include two approximately concentric partial circular shapes. One of the two approximately concentric partial circular shapes may include an omega shaped structure. The first conductive antenna element may be electrically coupled to the antenna feed through a feed via. The first conductive antenna element may be electrically coupled to the ground plane of the antenna through a one or more ground vias. In some embodiments, the close proximity to a wrist of the user may include a separation distance of less than 3 mm between the wrist of the user and the first and/or second conductive antenna elements.

According to various embodiments, the wearable wireless electronic device may include a conductive antenna element that may be electrically coupled to an antenna feed. The conductive antenna element may be in contact with and/or in close proximity to a user that is wearing the wearable wireless electronic device. The conductive antenna element may be configured to provide coupling between the user and the antenna such that the antenna resonates at a resonant frequency. The coupling between the user and the antenna may provide impedance matching to an antenna that comprises the conductive antenna element and the antenna feed. The impedance matching provided by the coupling between the user and the antenna may reduce return loss of the antenna. The wearable wireless electronic device may be worn on the wrist of the user. The conductive antenna element may reduce the impedance matching of the antenna when the wearable wireless electronic device is removed from contact with and/or the close proximity to the user. The conductive antenna element may prevent the antenna from resonating at the resonant frequency when the wearable wireless electronic device is removed from contact with and/or close proximity to the user.

According to various embodiments, the wearable wireless electronic device may include a case with a first face and a second face that opposes the first face. The first and second faces may define a periphery of the wearable wireless electronic device. A plurality of microelectronic devices may be included in the case. A first antenna element on the first face of the case and outside the case may conform to a portion of the periphery of the case. A second antenna element on the first face of the case and outside the case may extend from an edge of the first face of the case towards the center of the first face of the case. A feed via may extend from the first face of the case into the case and electrically connect the first antenna element to an antenna feed inside the case. A ground via may extend from the first face of the case into the case and electrically connect the second antenna element to a ground plane inside the case.

Other devices and/or operations according to embodiments of the inventive concept will be or become apparent to one with skill in the art upon review of the following drawings and detailed description. It is intended that all such additional devices and/or operations be included within this description, be within the scope of the present inventive concept, and be protected by the accompanying claims. Moreover, it is intended that all embodiments disclosed herein can be implemented separately or combined in any way and/or combination.

DETAILED DESCRIPTION

Figure 1:
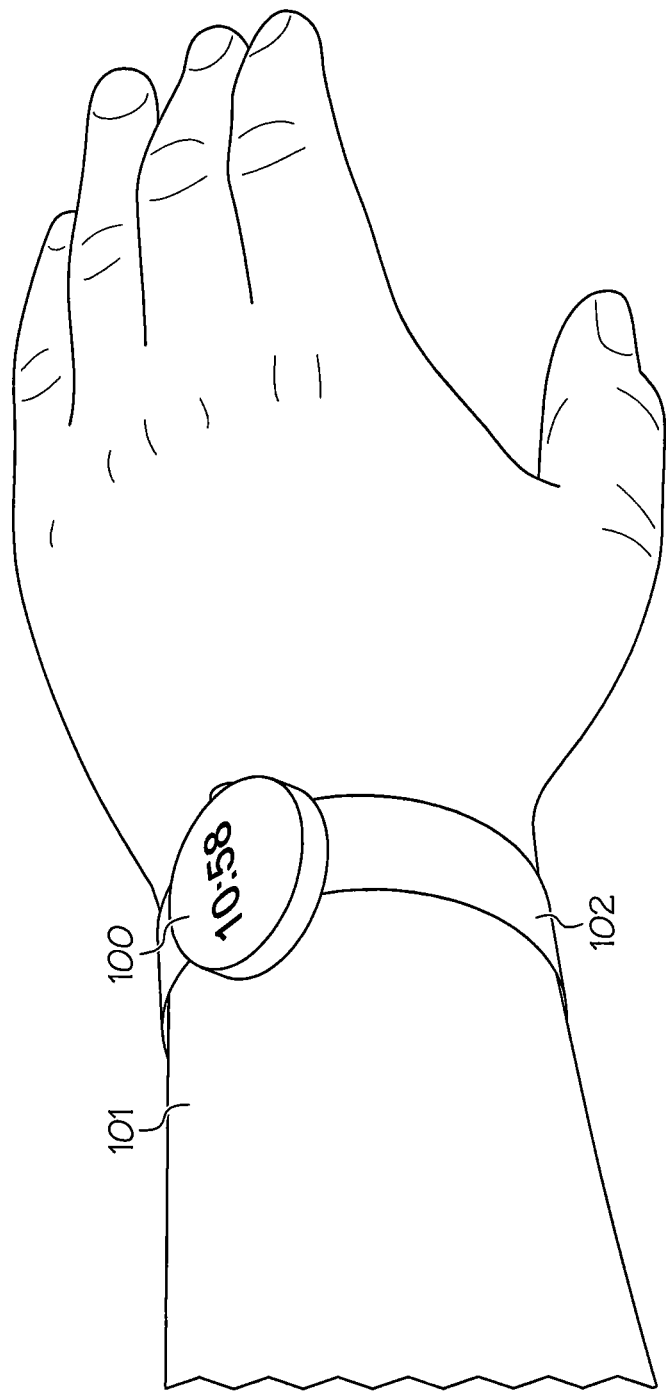
FIG. 1 illustrates a wrist of a human body with a wearable wireless electronic device, according to various embodiments of the present inventive concepts.

The present inventive concepts now will be described more fully with reference to the accompanying drawings, in which embodiments of the inventive concepts are shown. However, the present inventive concepts should not be construed as limited to the embodiments set forth herein. Rather, these embodiments are provided so that this disclosure will be thorough and complete, and to fully convey the scope of the embodiments to those skilled in the art. Like reference numbers refer to like elements throughout.

The terminology used herein is for the purpose of describing particular embodiments only and is not intended to be limiting of the embodiments. As used herein, the singular forms "a," "an," and "the" are intended to include the plural forms as well, unless the context clearly indicates otherwise. It will be further understood that the terms "comprises," "comprising," "includes," and/or "including,", and variants thereof, when used herein, specify the presence of stated features, steps, operations, elements, and/or components, but do not preclude the presence or addition of one or more other features, steps, operations, elements, components, and/or groups thereof.

It will be understood that when an element is referred to as being "coupled," "connected," or "responsive" to another element, it can be directly coupled, connected, or responsive to the other element, or intervening elements may also be present. In contrast, when an element is referred to as being "directly coupled," "directly connected," or "directly responsive" to another element, there are no intervening elements present. As used herein, the term "and/or" includes any and all combinations of one or more of the associated listed items.

Spatially relative terms, such as "above," "below," "upper," "lower," "top," "bottom," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly. Well-known functions or constructions may not be described in detail for brevity and/or clarity.

It will be understood that, although the terms "first," "second," etc. may be used herein to describe various elements, these elements should not be limited by these terms. These terms are only used to distinguish one element from another. Thus, a first element could be termed a second element without departing from the teachings of the present embodiments.

Unless otherwise defined, all terms (including technical and scientific terms) used herein have the same meaning as commonly understood by one of ordinary skill in the art to which these embodiments belong. It will be further understood that terms, such as those defined in commonly-used dictionaries, should be interpreted as having a meaning that is consistent with their meaning in the context of the relevant art and will not be interpreted in an idealized or overly-formal sense unless expressly so defined herein.

Antennas are commonly used in wearable wireless electronic devices such as mobile terminals or medical monitoring devices. Antenna designs may be compact in size and located inside the case of a wearable wireless electronic device. The antennas may be electrically isolated from the external surfaces of the case of the wearable wireless electronic device.

Conventionally, the body of the user degrades operation of antennas in wearable wireless electronic devices that are in contact with and/or in close proximity to the body of the user, due to absorption loss and/or poor impedance matching of the antenna to the circuits of the device. This poor impedance matching may result in higher signal losses and/or reduced efficiency of the antenna and/or radiation structure. Conventional wearable wireless electronic devices may actually perform better when removed from the close proximity of the user. Poorly impedance match antennas when worn by a user may not be suitable for radio antenna applications such as antennas for use in the 700 MHz to 2.5 GHz frequency range. These frequencies may be used for various types of communication in smart phones and medical monitoring devices such as LTE, GSM, GPS, PCS, UMTS, broadband internet access, Wi-Fi, Bluetooth, etc.

In sharp contrast, various embodiments of the inventive concepts may arise from the recognition that the user's body may be used to enhance performance of the antennas. More specifically, the antenna design of the wearable wireless electronic device may be improved by adding conductive antenna elements that are in contact with and/or in close proximity to the body of the user. The conductive elements may be coupled to the body of the user such that properties of the body may act as a conductor to provide impedance matching to the antenna and/or to improve the radiation efficiency. The coupling between the wrist of the user and the antenna may provide impedance matching to the antenna to improve the return loss and/or reduce the mismatch loss of the antenna when coupled to the wrist of the user. Proper impedance matching to the antenna allows the antenna to resonate at one or more resonant frequencies that may be used for communication. The properly matched antenna may in turn excite radiating currents in the ground plane structure of the device which in some cases may be the primary source of far-field radiation. Thus, antennas according to various embodiments of the inventive concepts may perform better when in contact with, or in close proximity to the body of the user.

Referring now to FIG. 1, the diagram illustrates a wrist 101 of a human body that is wearing a wearable wireless electronic device 100. As used herein, the term "wrist" may refer to the general area of the human body that includes the hand, palm, arm, and/or forearm. The wrist may include hair, skin aberrations, and other natural features. Although the embodiments discussed herein may be described in the context of the wrist of a human body, the wearable wireless electronic devices discussed herein may be worn near other parts of the human body such as around the neck, near the ear, around the head, near the waist or hips, around the torso, chest, fingers, legs, and/or ankles. Additionally, the embodiments described herein may be used with other non-human animals such as dogs, cats, horses, cows, etc. In some embodiments, the wearable wireless electronic device 100 may be fastened to the human body by a band 102. In some embodiments, the band may be nonconductive. Although the wearable wireless electronic device 100 is illustrated, for example, as a circular device similar to a watch, the device 100 may be of any shape such as a rectangle, oval, etc.

Figure 2:
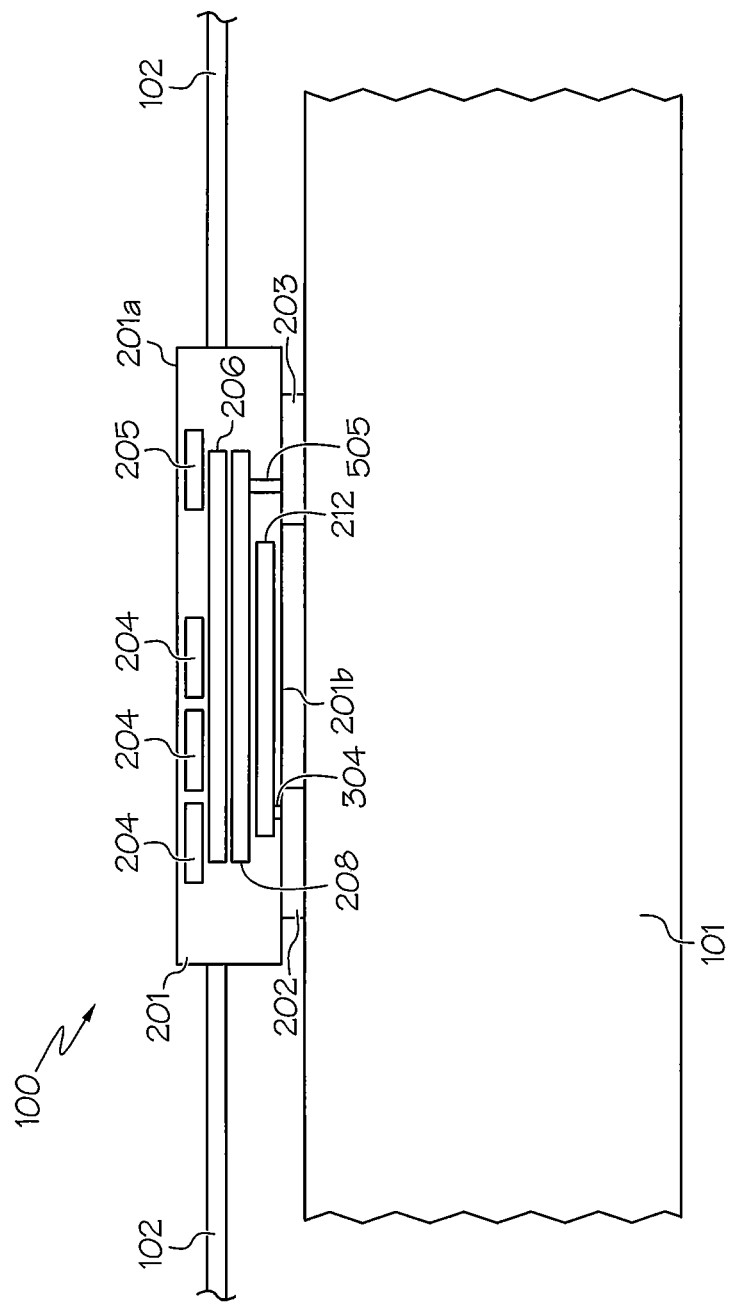
FIG. 2 illustrates a cross-sectional view of the wrist with the wearable wireless electronic device of FIG. 1, according to various embodiments of the present inventive concepts.

Referring now to FIG. 2, a cross-sectional view of the wearable wireless electronic device 100 on a wrist 101 of a user is illustrated. The wearable wireless electronic device 100 includes a case 201 that may include a plurality of microelectronic devices 204 in the case 201. The microelectronic devices 204 may provide various functionality to the wearable wireless electronic device, such as clocks, phones, heart monitors, breathing monitors, step and/or movement monitors, Wi-Fi, Bluetooth links, etc. The case 201 has a first face 201a and a second face 201b that is remote from the first face 201a. The second face 201b is adjacent to the wrist 101 of the user. The case may be made of a conductive metal material and/or may be made of a non-conductive material. The first face 201a may include a touch screen interface and/or control elements. In some embodiments, the second face 201b of the case 201 may be non-conductive or may have an outer wrapping of non-conductive material such as rubber or plastic. The wearable wireless electronic device 100 may include a first conductive antenna element 202 and a second conductive antenna element 203, that are outside the case 201. The first and second conductive antenna elements 202 and 203 may protrude from the second face 201b of the case 201 toward the wrist 101 of the user. The first and second conductive antenna elements 202 and 203 may be in direct contact with the wrist of the user as illustrated in FIG. 2. In some embodiments, the first and second conductive antenna elements 202 and 203 may in close proximity (<5 mm) of the wrist of the user, for example, due to presence of a dielectric covering, skin aberrations, presence of hair on the wrist of the user, bone structure, and/or other types of coverings on the wearable wireless electronic device 100.

Figure 3:
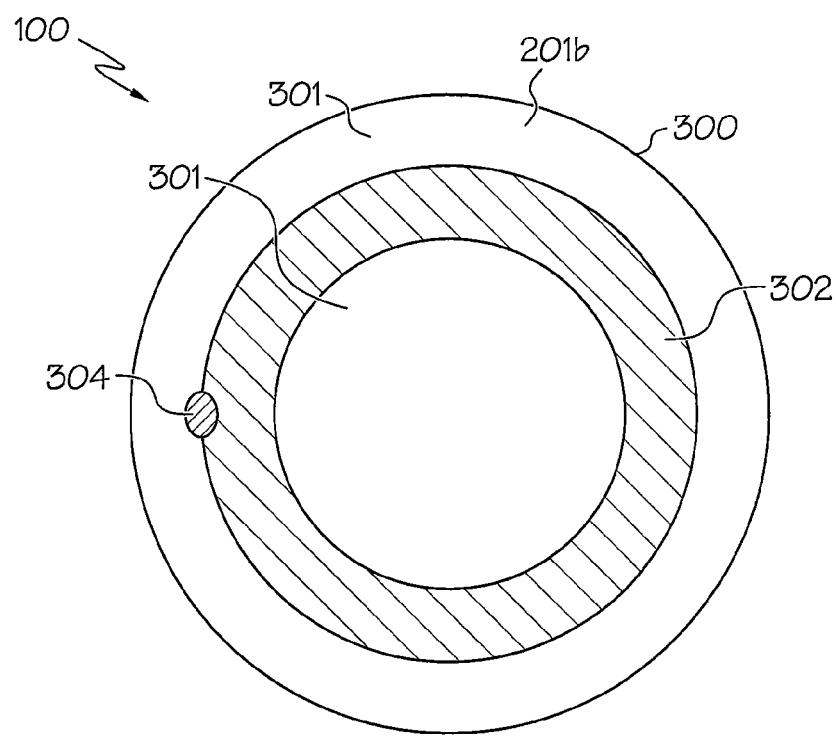
FIGS. 3 and 4 illustrate antenna elements on a face of the wireless electronic device of FIGS. 1 and 2 for a single-band resonance antenna, according to various embodiments of the present inventive concepts.

The conductive antenna elements 202 and 203 of the wearable wireless electronic device 100 may have different configurations and shapes to produce various resonance frequencies as illustrated in FIGS. 3-8. FIGS. 3-8 illustrate the wearable wireless electronic device 100 but do not illustrate the armband 102 of FIGS. 1 and 2. Referring now to FIG. 3, a wireless electronic device 100 including an antenna 300 with antenna elements on the second face 201b of the wearable wireless electronic device 100 of FIGS. 1 and 2 is illustrated. In this non-limiting example, the antenna 300 may have a single band of resonance and bandwidth efficiency of about −12 dB when this device 100 is placed on the wrist. For example, the antenna 300 may operate in the highband frequencies at Bluetooth and/or Wi-Fi frequencies in the range 2.4 GHz to 2.485 GHz. This highband resonance maybe achieved by a conductive metal antenna element 302 in the shape of a ring on the second face 201b of the wearable wireless electronic device 100 that is placed in contact with an/or in close proximity to the wrist of the user's body. The dimensions of the ring may determine the resonance frequency of the antenna. For example, the outer diameter of the conductive metal antenna element 302 may be 30 mm and the inner diameter of the conductive metal antenna element 302 may be 20 mm to provide a width of about 5 mm for the conductive metal antenna element 302 on the second surface 201b. The conductive metal antenna element 302 may be on a non-conductive surface 301 such as plastic on the wearable wireless electronic device 100. A feed via 304 may extend through the second face 201b from the conductive antenna element 302 into the wearable wireless electronic device 100. The feed via 304 may be a conductive structure and/or a spring contact. The length of the feed via 304 may be reduced to mitigate the inductance of the feed via 304. In the event that the circuitry contained on the printed circuit board 206 is not proximate to the feed via 304, a coaxial structure contained in, for example, a flexible printed circuit board 206 may extend from the feed via 304 around a battery 205 to one or more microelectronic devices 204 inside the case of the wearable wireless electronic device 100. In some embodiments, the printed circuit board 206 may include a ground plane 208 inside the case 201. A ground via 505 may electrically connect the second conductive antenna element 203 to the ground plane 208 of the wearable electronic device 100 in the case 201. The flexible printed circuit board 206 may provide a low loss, thin structure that reduces the length of the feed via 304. In some embodiments, the antenna element 302 may have a separation of 0.5 mm to 2 mm from other conductive elements such as the battery of the wearable wireless electronic device 100.

Figure 4:
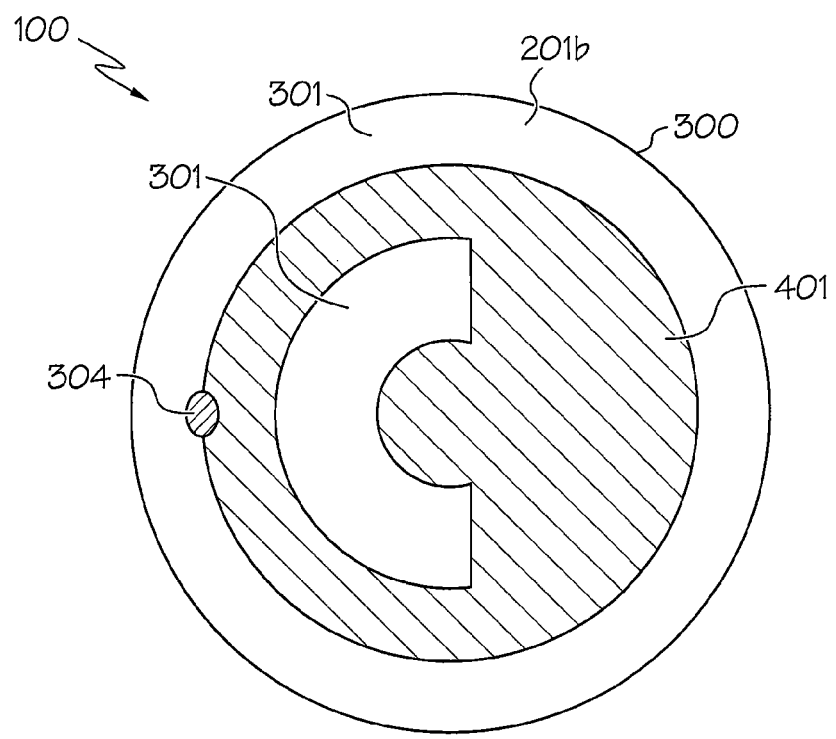

Referring now to FIG. 4, an antenna 300 with a different shape antenna element when compared to FIG. 3, on the face 201b of the wearable wireless electronic device 100 of FIGS. 1 and 2, is illustrated. The antenna element 401 with a rainbow-shaped void may achieve a wide bandwidth resonance from about 1.5 GHz to 2.4 GHz. In this non-limiting example, the antenna 300 may achieve a single band of resonance and wide bandwidth with efficiency of about −14 dB in the GPS frequency range and/or an efficiency of about −13 dB in the Bluetooth frequency range when this wearable wireless electronic device 100 is placed on the wrist. In some embodiments, the void of antenna element 401 may be between 4 mm and 5.5 mm wide between the upper branch and lower circular area of antenna element 401. The outer diameter of the non-conductive surface 301 may be about 34 mm. The outer diameter of the antenna element 401 may be about 28 mm and the inner diameter of the void may be about 20.5 mm.

Figure 5:
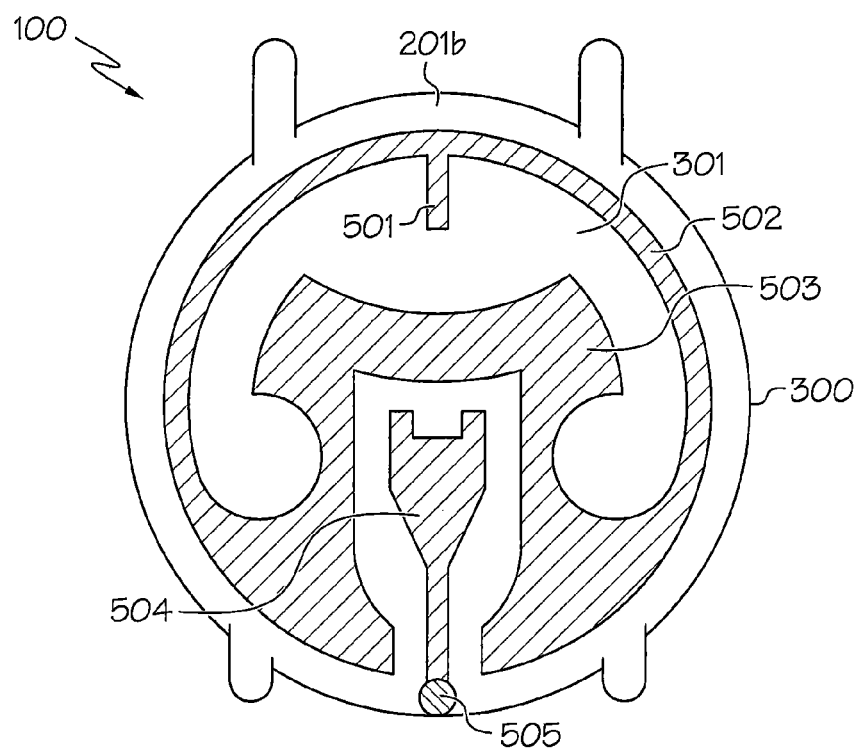
FIGS. 5-8 illustrate antenna elements on a face of the wireless electronic device of FIGS. 1 and 2 for a multi-band resonance antenna, according to various embodiments of the present inventive concepts.

In order to achieve suitable performance in the lowband frequencies, it may be desirable to extend the ground plane that is inside the case 201 to outside the case 201 of the wearable wireless electronic device 100. A first conductive antenna element such as antenna element 302 of FIG. 3 and/or antenna element 401 of FIG. 4 may serve as a first conductive antenna element that provides the radiating function of antenna 300. The radiating function of the antenna may come from both the antenna 300 and from the ground plane that is inside the case 201. When the antenna is in contact with or in close proximity to the user's body, the bulk of the far-field radiation may result from the radiating ground plane. A second conductive antenna element that may include a parasitic element on the surface 201b which couples to the ground plane inside the case 201 and may serve to extend the ground plane. This extending of the ground plane may, in turn, provide some blocking and directivity of the radiating structure comprising the antenna 202, ground plane of the printed circuit board 206, and the ground plane extension 203. A single contact location that extends from the ground plane that is inside the case 201 to the conductive antenna element may provide the aforementioned blocking and directivity functions. Referring now to FIG. 5, the antenna 300 may include a first conductive antenna element 502 and a second conductive antenna element 504 on a face 201b of the wearable wireless electronic device 100 of FIGS. 1 and 2. The second conductive antenna element 504 may be a parasitic element or ground plane extension that connects to the ground plane inside the case 201. A ground via 505 may electrically connect the second conductive antenna element 504 to a ground plane of the wearable wireless electronic device 100 in the case 201. The second conductive antenna element 504 may be fork-shaped and/or inverted triangle-shaped. The second conductive antenna element 504 may behave as an extension of the ground plane and provide lowband improvements. The first conductive antenna element 502 may include one or more approximately circular shapes along and edge of the outside surface of the wireless electronic device 100. The first conductive antenna element 502 may include an inner conductive antenna portion 503 that is shaped similar to the Greek letter omega and/or as a bat-wing-shape. The first conductive antenna element 502 may be electrically coupled to the antenna feed 212 of the antenna 300 through a feed via 501. Current may flow in at least a portion of the first conductive antenna element 502. More current may flow in the top portion of the loop of the first conductive antenna element 502 when compared to the bottom portion of the loop of the first conductive antenna element 502.

Figure 6:
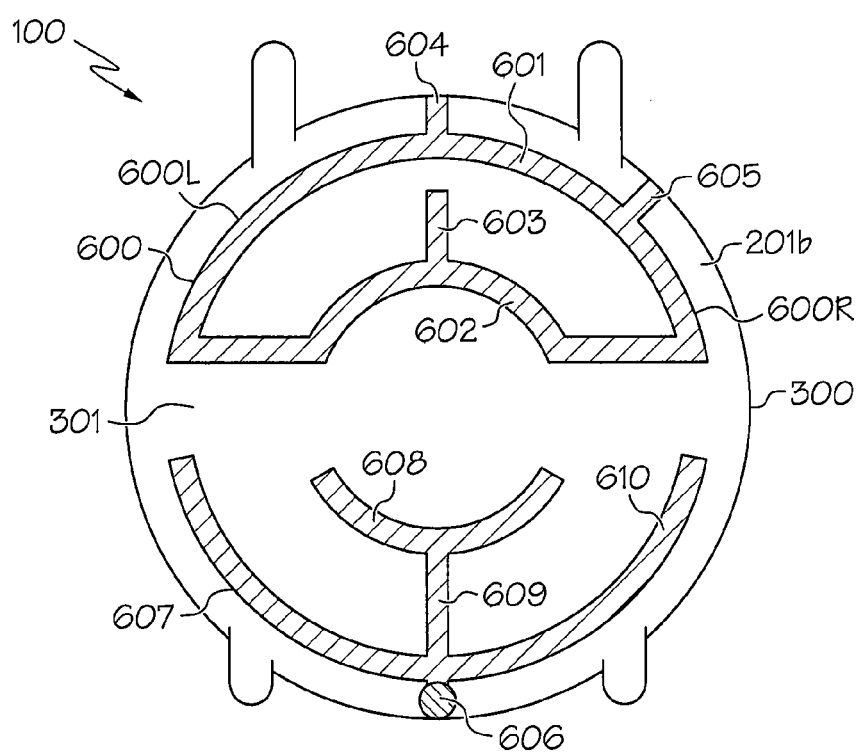

In some embodiments, the feed element of the antenna may be electrically connected to a ground plane in two or more different points to achieve a broader highband frequency response. Coupling to the ground plane in this manner may improve highband performance of the antenna. Referring now to FIG. 6, a wearable wireless electronic device 100 is illustrated that includes a first conductive antenna element 600 and a second conductive antenna element 607. When compared to the antenna design of FIG. 5, the parasitic branch 609 has been shortened and distanced from the first conductive antenna element 600. The first conductive antenna element 600 may be connected to an antenna feed of an antenna through a feed via 603. The first conductive antenna element 600 may be electrically connected to the ground plane of the wearable wireless electronic device 100 by one or more ground vias 604 and 605. For example, as illustrated in FIG. 6, the first conductive antenna element 600 may be connected to the ground plane of the wearable wireless electronic device 100 through ground vias 604 and 605. Ground via 604 may improve performance in the lower part of the highband frequencies for applications such as GPS. Ground via 605 may improve performance in the higher part of the highband frequencies for applications such as Bluetooth. The first conductive antenna element 600 may include two or more approximately concentric partial circular shapes. Still referring to FIG. 6, for example, the first conductive antenna element 600 may include a partial circular shape 601 along an edge of the wearable wireless electronic device 100 and another partial circular shape 602 that is spaced apart from the partial circular shape 601. The partial circular shapes of the first conductive antenna element 600 are connected to one another to provide a loop structure. The left portion 600L of the loop of the first conductive antenna element 600 may resonate in the lower part of the highband frequencies for applications such as GPS. The right portion 600R of the loop of the first conductive antenna element 600 may resonate in the higher part of the highband frequencies for applications such as Bluetooth.

Still referring to FIG. 6, the parasitic structure 609 of the second conductive antenna element 607 may enhance lowband frequency performance in the range of 700 MHz-1000 MHz. The second conductive antenna element 607 may include one or more concentric hollow half moon-shaped elements 608 and/or 610. The second conductive antenna element 607 may be electrically coupled to a ground plane of the wearable wireless electronic device 100 through a coupling via 606. In some embodiments, the second conductive antenna element 607 may be lengthened and positioned closer to the first conductive antenna element 600 to improve performance. However, as the second conductive antenna element 607 is moved closer to the first conductive antenna element 600, energy from the highband resonance frequencies may couple to the second conductive antenna element 607, i.e. parasitic, which may decrease the radiation efficiency of the structure, negatively affecting the performance at the highband resonance frequencies.

Figure 7:
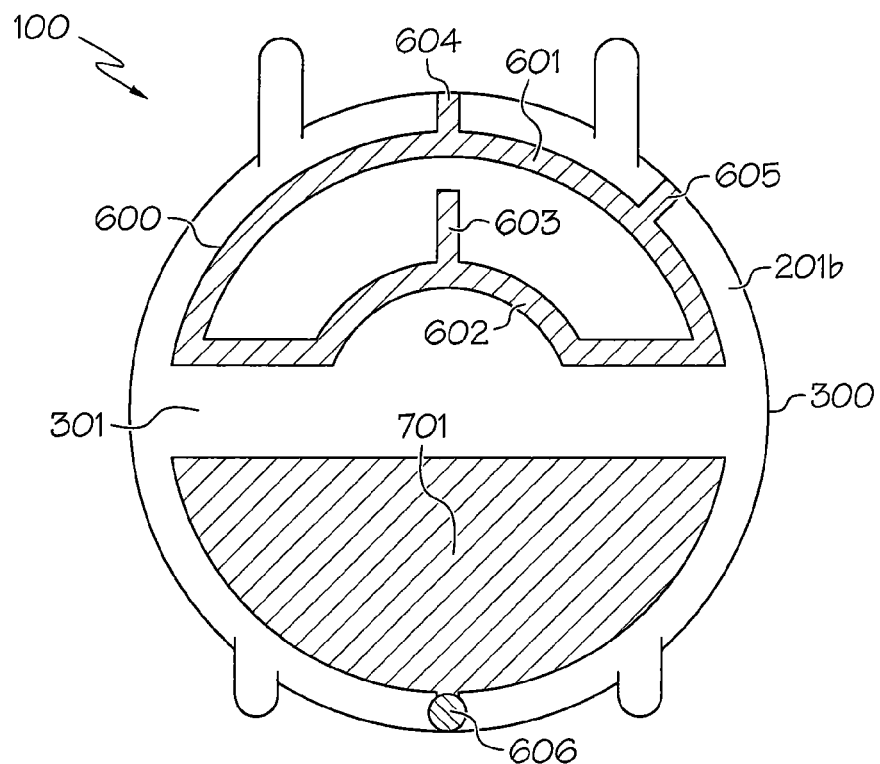

Referring now to FIG. 7, an antenna structure similar to FIG. 6 is illustrated. The second conductive antenna element 701 may be a filled half moon-shaped structure. In some embodiments, the filled half moon shape of the second conductive antenna element 701 may be a ground plane extension that achieves better performance at some of the lowband frequencies. In some embodiments, the filled half moon shape of the second conductive antenna element 701 may be replaced by a half moon shape with a void, similar to the rainbow-shaped void in antenna element 401 of FIG. 4. In some embodiments, the ground plane extension of the second conductive antenna element 701 may not be very active when the highband is active in the 1.5 GHz to 2.5 GHz range.

Figure 8:
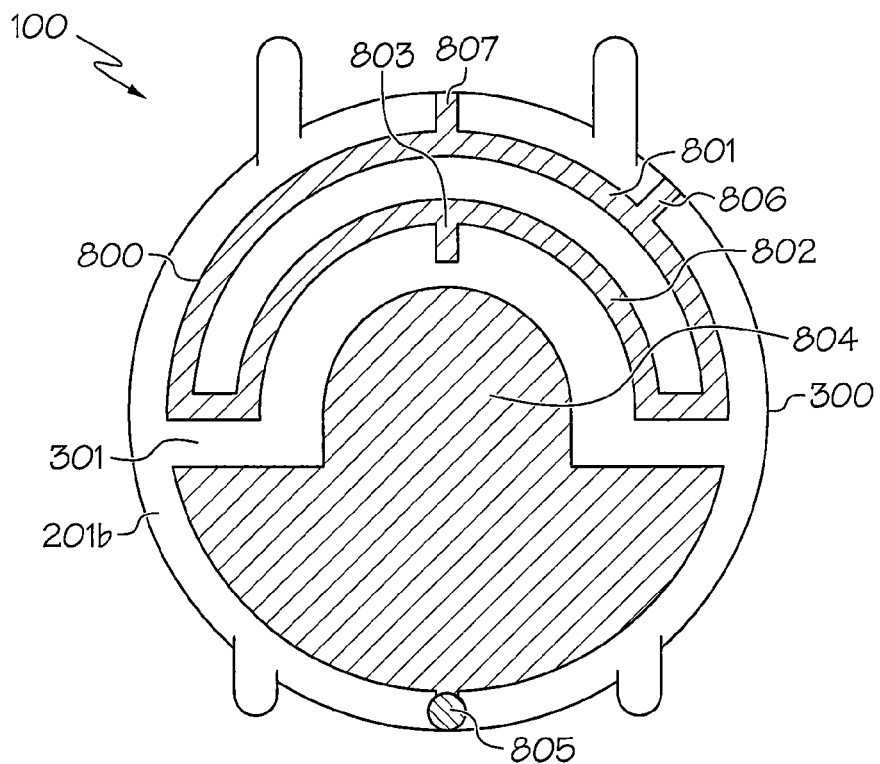

Referring now to FIG. 8, the concentric branches 801 and 802 of first conductive antenna element 800 are spaced closer together and are closer to the edge of the wearable wireless electronic device 100 when compared to the antenna structures of FIGS. 6 and 7. The second conductive antenna element 804 may be a filled moon-shaped structure with a smaller rising sun-shaped structure. In this configuration, the highband performance may be slightly degraded when compared to the devices of FIGS. 6 and 7. However, the lowband performance may be improved over the devices of FIGS. 6 and 7. For example, −12 dB efficiency may be achieved at 700 MHz (band 17) and −7 dB may be achieved in the 850 MHz band. In some embodiments, the ground plane extension of the second conductive antenna element 804 may be active in the lowband frequencies due to coupling to the ground plane of the printed circuit board 206 and not due to coupling between this ground plane extension and the first conductive antenna element 800 that serves as the main antenna radiator. In some embodiments, the filled moon-shaped structure with the rising sun-shaped structure of the second conductive antenna element 701 may be replaced by a half moon shape with a void, similar to the rainbow-shaped void in antenna element 401 of FIG. 4, but may also include the rising sun-shaped structure.

Performance of the wearable wireless devices 100 of FIGS. 3-8 may be measured based on the CTIA Test Plan for Wireless Device Over-the-Air Performance using body phantoms with material properties similar to those specified for the phantom hands in this test plan. Test results may be compared to conventional devices with antennas in the armband or against typical Cellular Operator requirements for phones tested in the Beside Head and Hand (BHH) test position. As discussed herein, the terms "armband" and "wristband" are used interchangeably for a band used to attach the wearable wireless electronic device 100 to the body. A disadvantage of the conventional antennas in the armband is that users may wish to have inexpensive options for changing the armband. Further disadvantages of armband antennas may be cost, limited availability of options such as colors, materials, etc., inability to have a metal band if the antenna is in the armband, possible inability to use leather due to water absorption and durability issues, band flexibility since the armband tends to be stiffer with an antenna included, etc. Additional disadvantages of armband antennas may include problems with logistics and/or availability of replacement parts. Additionally, usage wear based on the user sweating, flexing the armband, or otherwise damaging the armband may affect performance of the armband antenna. The above antenna designs however were benchmarked against a 20 mm×15 mm armband antenna with meandered monopoles without a ground in the wristband and with about 5 mm separation to the arm. The above antenna designs were also compared to typical operator performance expectations as well as in different positions of the user's wrist as well as when the device is not in the proximity of the user. These test results will now be discussed in detail.

Figure 9:
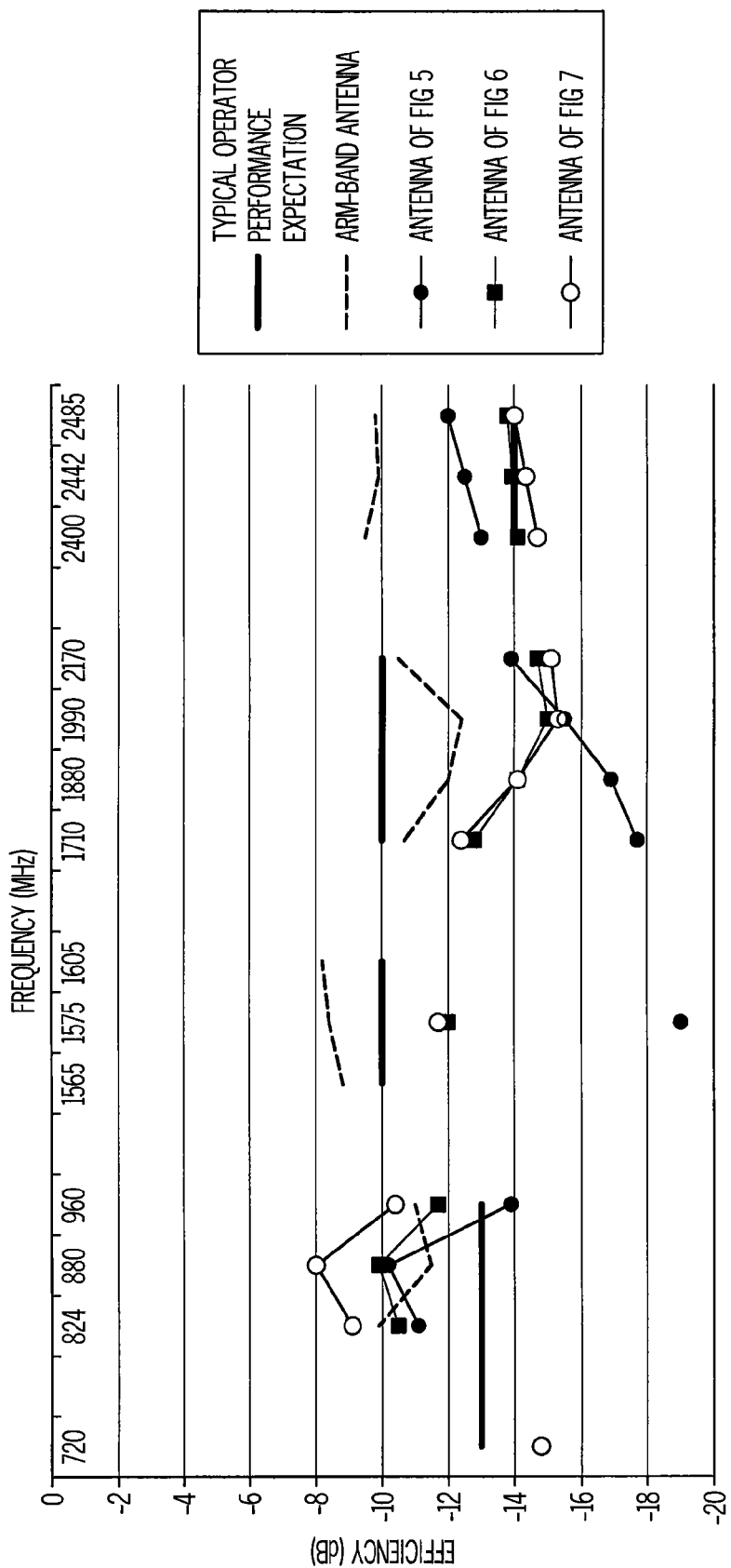
FIGS. 9-10 illustrate the efficiency measurements in dB of various antenna configurations in the body worn wireless electronic device of FIGS. 5-7, according to various embodiments of the present inventive concepts.

Referring now to FIG. 9, results of testing of various antenna structures across different frequency bands is graphically illustrated. The vertical axis or y-axis of the graph of FIG. 9 represents the efficiency in dB, i.e. the average gain, of the antenna. The horizontal axis or x-axis represents different frequencies for which the antenna designs were tested, ranging from about 700 MHz to 2.5 GHz. For example, lowband frequencies used in applications such as LTE and GSM in the range between 700 MHz-1000 MHz are illustrated. As seen from the graph, the antennas of FIGS. 5-7 when in contact with and/or in close proximity to the user, perform better than the typical operator performance expectation in the lowband frequencies. However, the antennas of FIGS. 5-7 appear to perform below the typical operator performance expectation for frequencies between 1500 MHz-2200 MHz. As such, these antennas may not be as well suited for applications at these frequencies such as GPS or UMTS, which are in the 1500 MHz-2200 MHz frequency range. The antennas of FIGS. 5-7 perform better than the typical operator performance expectation in the frequency range between 2.4 GHz-2.5 GHz. As such, these antennas appear to be suitable for applications at these frequencies such as Bluetooth, which are in the 2.4 GHz-2.5 GHz range. In other words, as illustrated by FIG. 9, the antennas of FIGS. 5-7 appear to provide suitable performance when the antennas are in contact with and/or in close proximity to the wrist of the user.

The Typical Operator Performance Expectation of FIG. 9 represents the performance request and/or requirements for operators for hand-held cellular devices. This is used as a benchmark for comparative purposes only since there standard requirements from operators for wrist worn devices are not yet available. Since the overall size of the device for wrist-worn devices may be smaller than a typical hand-held cellular device, the performance requirements from operators for wrist-worn devices may be lower. Hence, the operator benchmark of hand-held devices may be 2 dB to 4 dB below performance level illustrated in FIG. 9.

Figure 10:
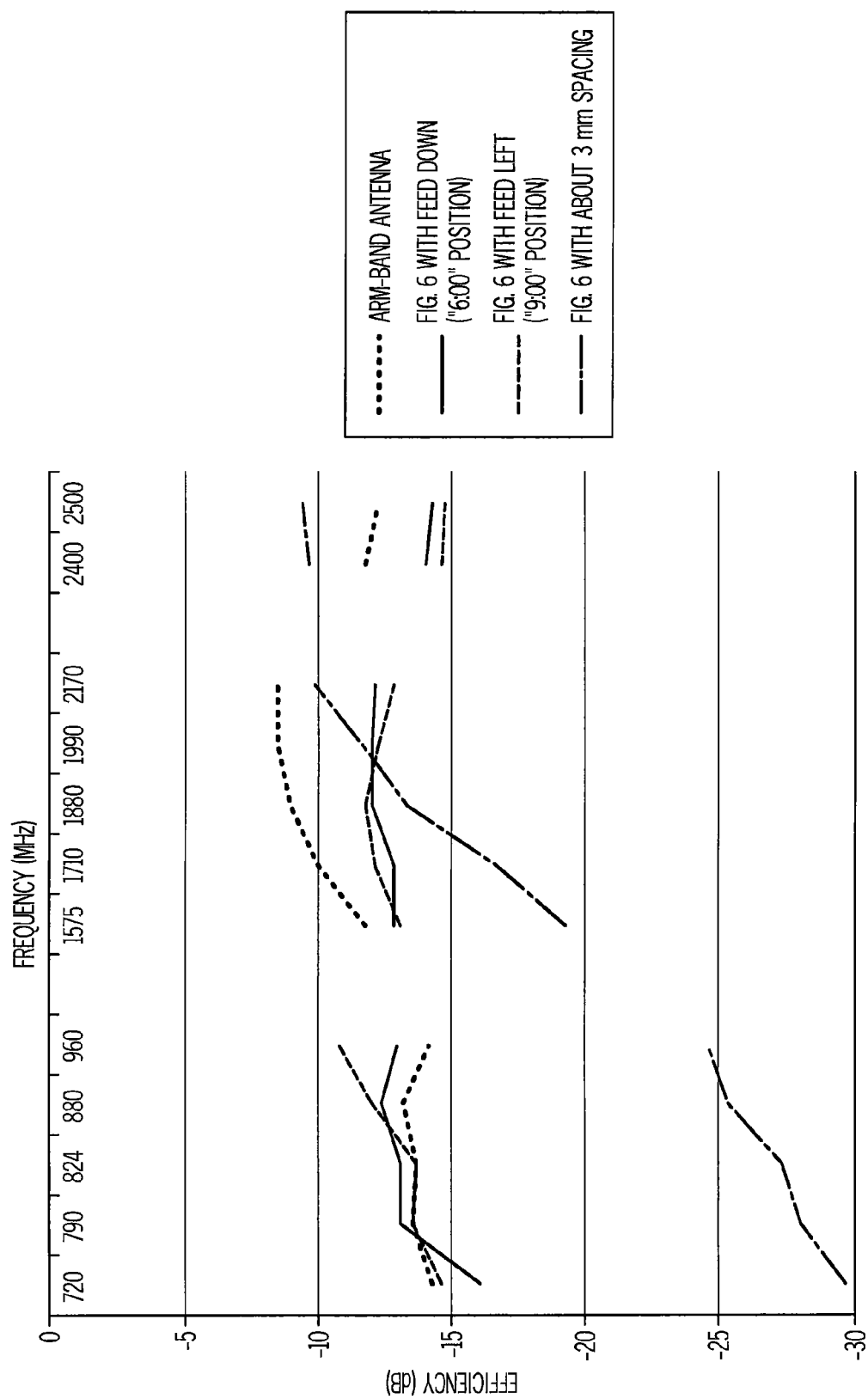

Referring now to FIG. 10, results of testing of various antenna structures across different frequency bands is graphically illustrated. The y-axis of the graph of FIG. 10 represents the efficiency in dB, i.e. the average gain, of the antenna. The x-axis represents different frequencies for which the antenna designs were tested, ranging from about 700 MHz to 2.5 GHz. The data in this graph represents testing of a wristband antenna, the antennas of FIG. 6 with the feed 603 oriented in different positions with less than 3 mm spacing from the wrist, and the antenna of FIG. 6 at about 3 mm spacing from the wrist. In some embodiments described herein, the antennas may perform better in some orientations on the wrist. Performance may vary based on some of the non-symmetric properties of the human wrist and a variety of wearing methods. For example, performance of the wearable wireless electronic device 100 may be based on factors such as bone structure, bone density, dielectric properties of the skin, blood, bones, muscles, tendons, etc. As discussed herein, the "6 o'clock position" refers to the wearable wireless electronic device 100 of FIG. 6 rotated such that the feed via 603 is oriented downward on the page. In other words, if the wearable wireless electronic device 100 of FIG. 6 is worn on the backside of a wrist similar to a traditional watch, the feed via 603 would be in the "6 o'clock position". The "9 o'clock position" refers to the device 100 rotated such feed via 603 is oriented to the left of the page. As seen from the graph of FIG. 10, the antenna of FIG. 6 performs better than the wristband antenna in the lowband frequencies when less than 3 mm from the wrist at either the 6 o'clock or 9 o'clock positions. However, the antenna of FIG. 6 appears to perform worse than the wristband antenna for frequencies between 1500 MHz-2200 MHz. As such, these antennas may not be as well suited for applications at these frequencies such as GPS or UMTS. The antenna of FIG. 6 with about a 3 mm spacing from the wrist performs better than the wristband antenna in the frequency range between 2.4 GHz-2.5 GHz. As such, these antennas appear to be suitable for applications at these frequencies such as Bluetooth when worn comfortably by the user with about 3 mm spacing. Furthermore, as illustrated by FIG. 10, the wearable wireless electronic device 100 appears to show provide good performance when the first and second conductive antenna elements 600 and 607 are in contact with and/or in close proximity to the wrist of the user. Additionally, although the results of FIG. 10 are discussed with respect to the antenna 300 of FIG. 6, similar test results were obtained for the antenna 300 of FIGS. 7 and 8. Therefore, the conclusions discussed above regarding frequency ranges with respect to the antenna 300 of FIG. 6 may also apply to the antenna 300 of FIGS. 7 and 8.

Figure 11:
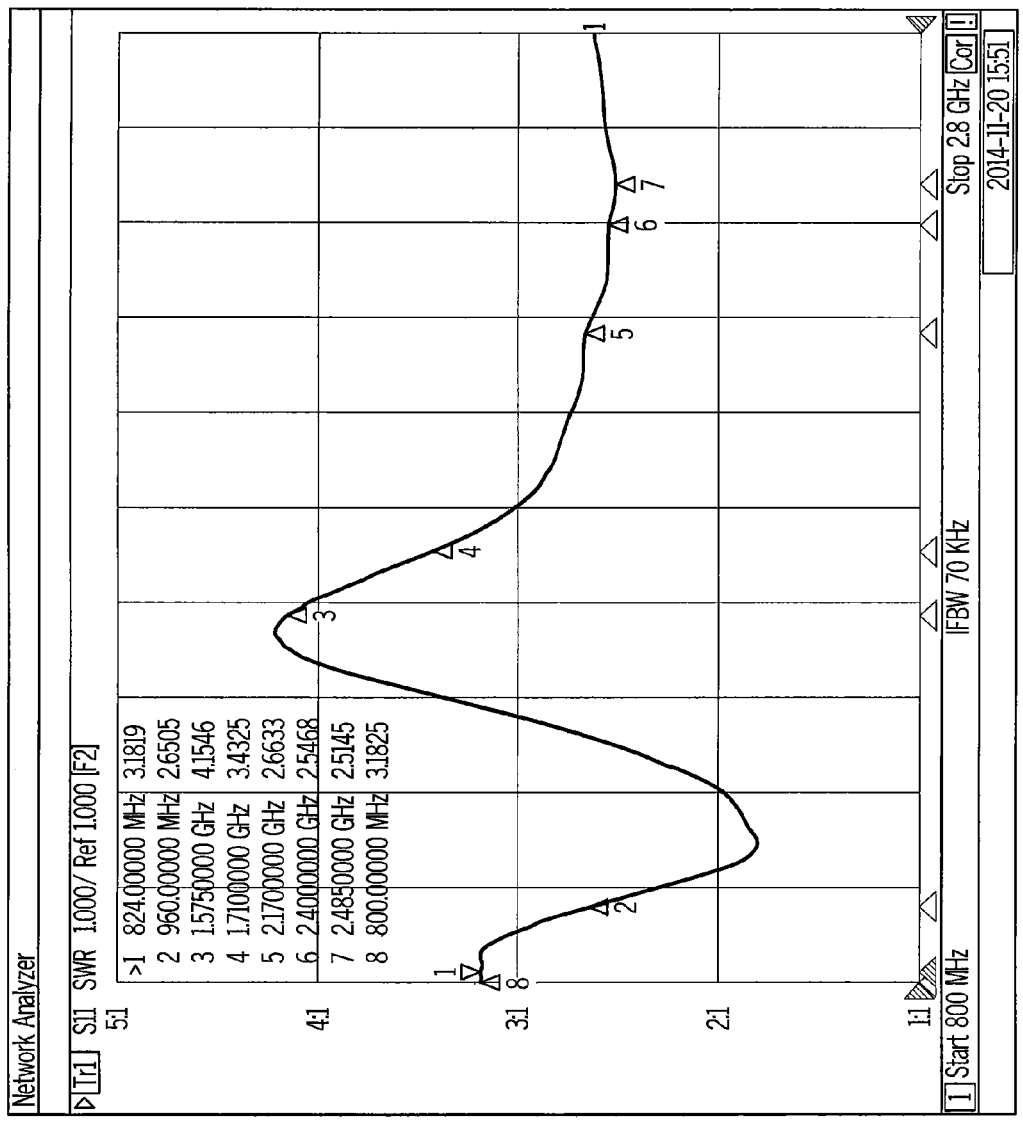
FIGS. 11-13B illustrate the measured standing wave ratio at various frequencies for the antenna elements of FIG. 6 at various positions on the user's wrist, according to various embodiments of the present inventive concepts.

FIGS. 11-13B illustrate the standing wave ratio at various frequencies for the antenna elements of FIG. 6 at various positions on the user's wrist. A standing wave ratio of 1:1 indicates perfect 50 ohm impedance matching of the associated circuits of the antenna 300. Although impedance matching is described in the context of 50 ohm impedance matching as a non-limiting example, non-50 ohm impedance matching may be applied to the present inventive concepts. A standing wave ratio less than 3:1 may be considered suitable for communication at a given frequency using the antenna 300. Referring now to FIG. 11, the standing wave ratio for a wearable wireless electronic device 100 including the antenna 300 of FIG. 6 when worn in a position that is comfortable for a user, that is not tight enough to place significant pressure on the wrist of the user, but within 3 mm of the body is illustrated. The antenna in this scenario appears to be suitable for communications in the lowband frequencies and the upper range of the highband frequencies since the standing wave ratio is below 3:1 in these ranges. In other words, as illustrated by FIG. 11, the wearable wireless electronic device 100 appears to provide suitable performance when the first and second conductive antenna elements 600 and 607 are in contact with and/or in close proximity to the wrist of the user.

Figure 12:
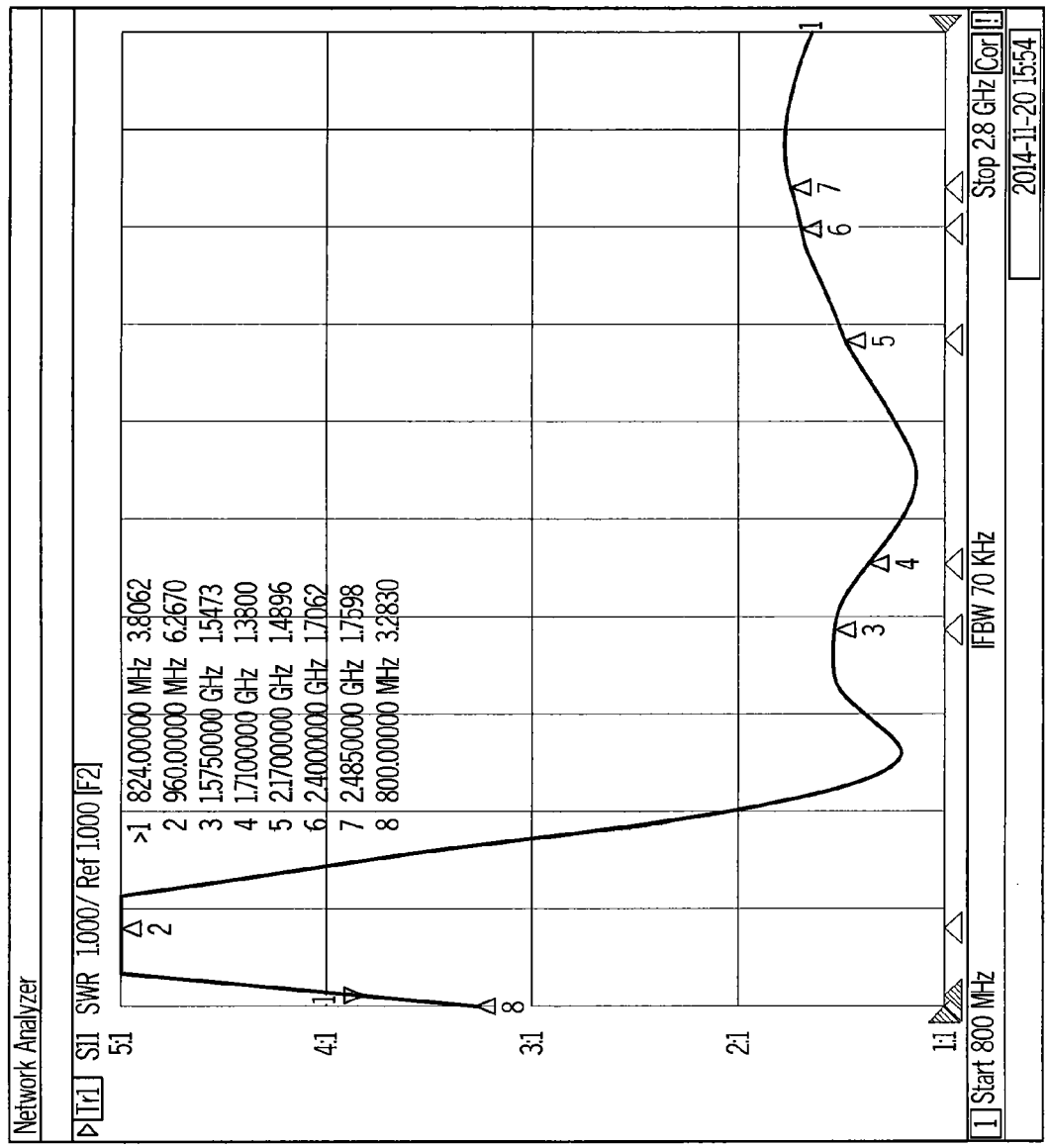

Referring now to FIG. 12, the standing wave ratio for a wearable wireless electronic device 100 including the antenna 300 of FIG. 6 when worn in a position that is tight enough on the wrist to place moderate pressure on the wrist of the user is illustrated. In this case, the first conductive antenna element 502 and the second conductive antenna element 504 of the antenna 300 of FIG. 6 may be in direct contact with the wrist of the user. In this position, this antenna appears to possess excellent matching characteristics at frequencies approximately above 1000 MHz. Hence the antenna 300 of FIG. 6 may be suitable for communication at frequencies above 1000 MHz for applications such as GPS, PCS, Wi-Fi, and/or Bluetooth.

Figure 13A:
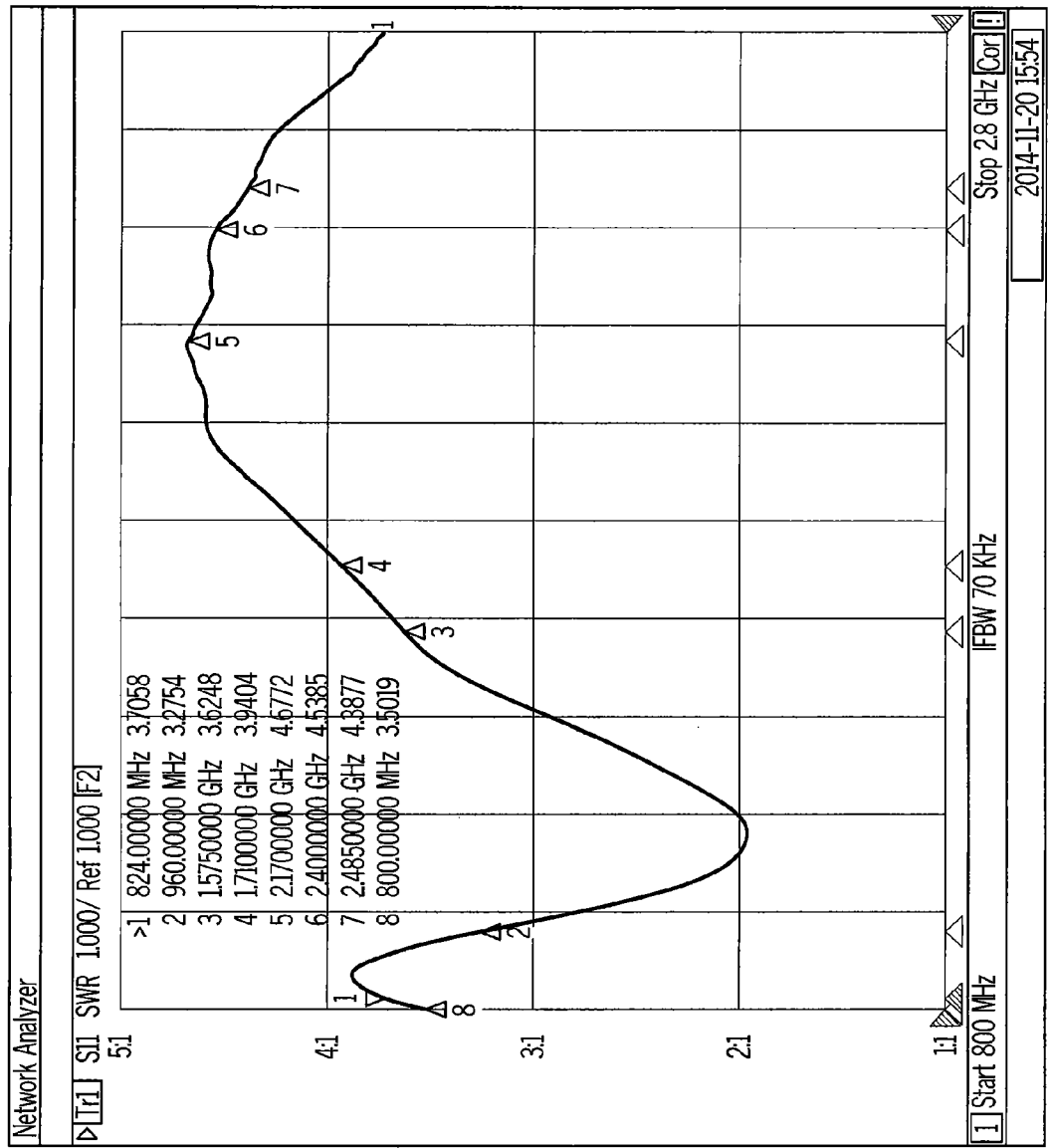

Referring now to FIG. 13A, the standing wave ratio for a wearable wireless electronic device 100 including the antenna 300 of FIG. 6 when worn very loosely on the wrist of the user is illustrated. In this case, the first conductive antenna element 502 and the second conductive antenna element 504 of the antenna 300 of FIG. 6 may be about 3 mm from the wrist of the user. The standing wave ratio of this antenna is less than 3:1 approximately between 1 GHz-1.5 GHz. The impedance matching at frequencies greater than 1.5 GHz appears to be poor when the wearable wireless electronic device is worn in this position.

Figure 13B:
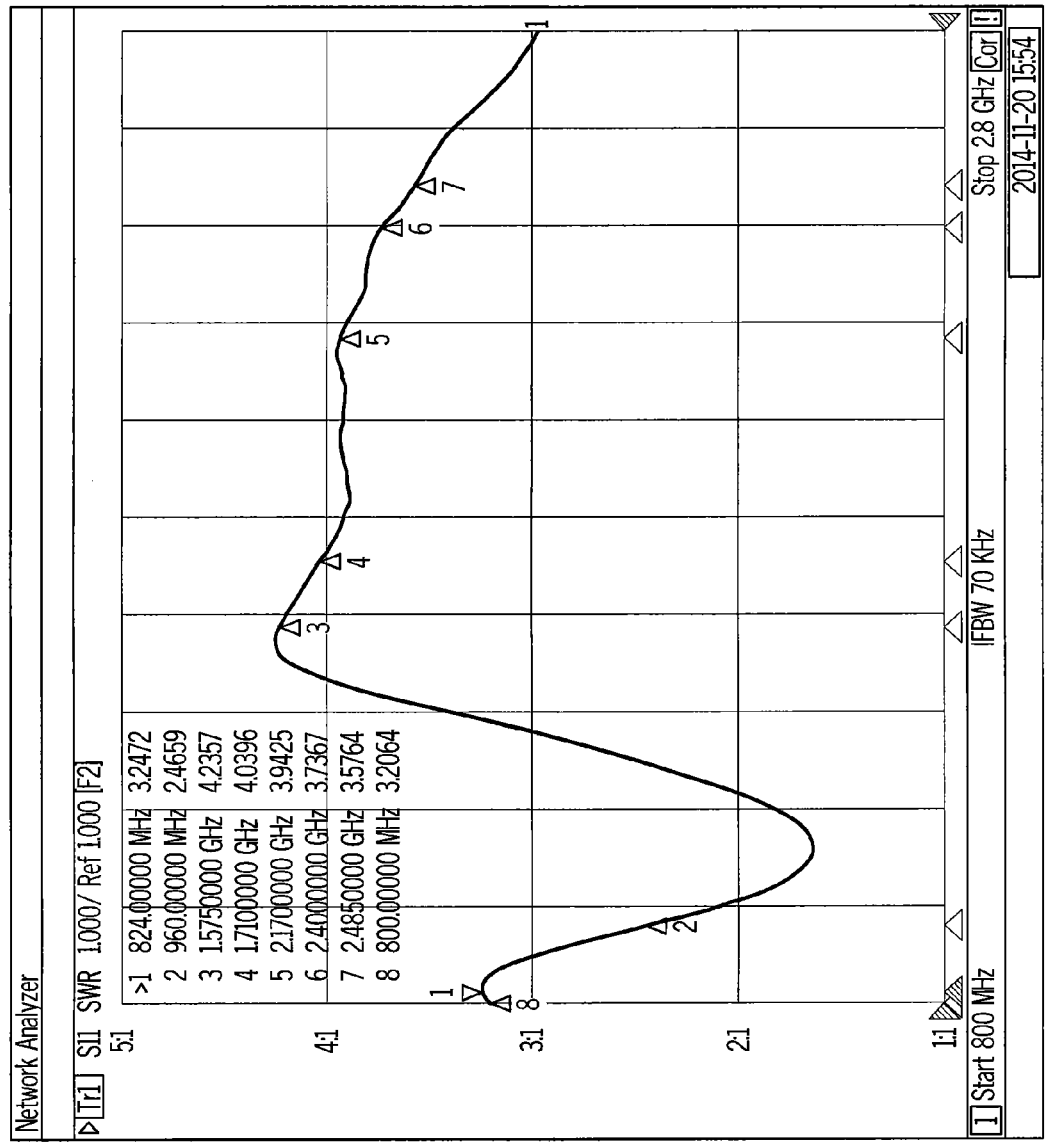

Referring now to FIG. 13B, the standing wave ratio for a wearable wireless electronic device including the antenna 300 of FIG. 6 when worn very loosely on the wrist of the user is illustrated. In this case, the first conductive antenna element 502 and the second conductive antenna element 504 of the antenna of FIG. 6 may be about 3 mm from the wrist of the user, but slightly tilted towards the side of the arm when compared to the scenario of FIG. 13A. The standing wave ratio of this antenna is less than a ratio of 3:1 in a frequency band approximately between 850 MHz-1.0 GHz, which appears to be a narrower band compared to the graph of FIG. 13A. The impedance matching at frequencies greater than 1.0 GHz appears to be poor when the wearable wireless electronic device is worn in this position.

Figure 14:
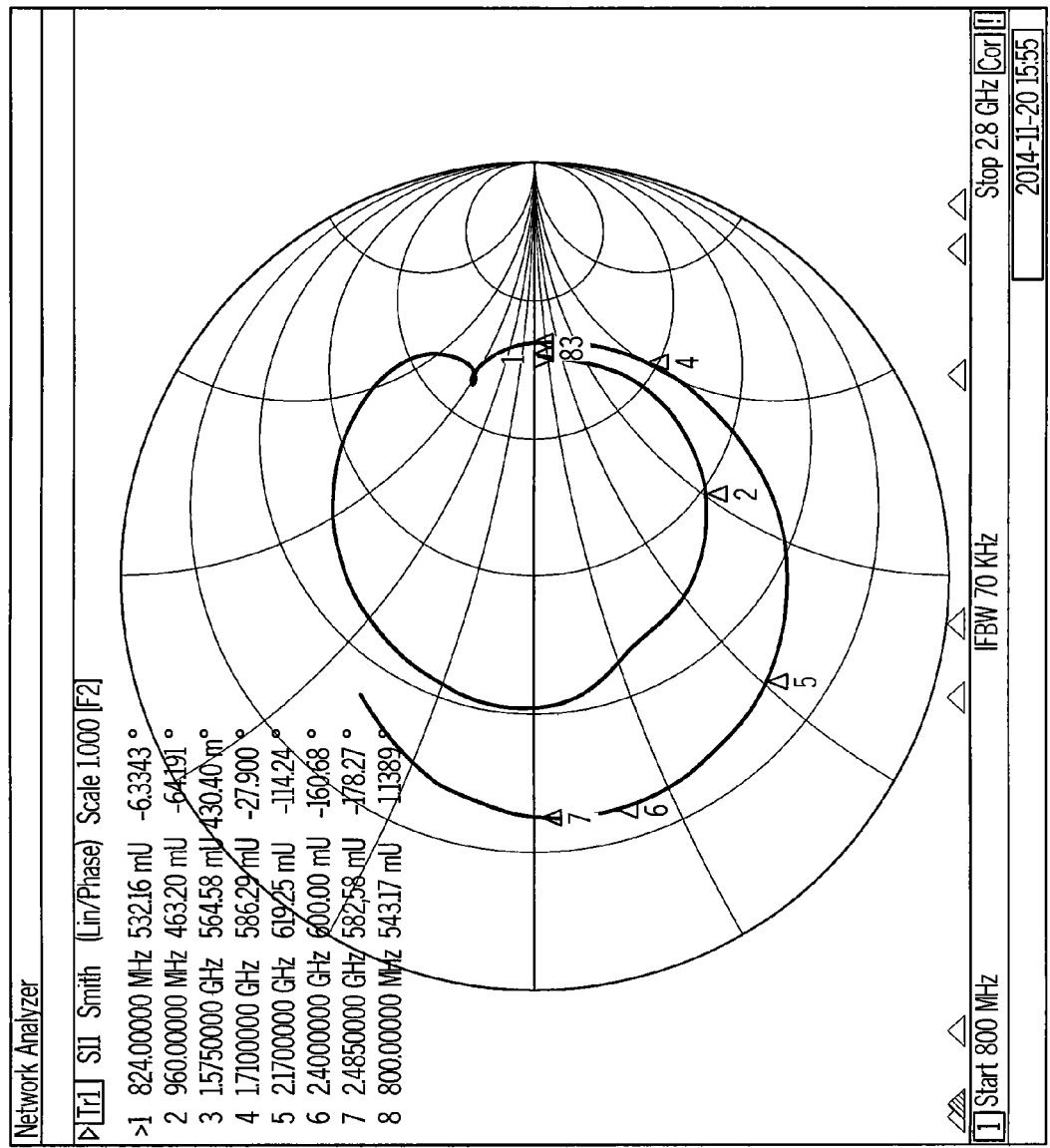
FIG. 14 illustrates a measured Smith chart at various frequencies of the antenna elements of FIG. 6 on a user's wrist.

Referring now to FIG. 14, a Smith chart at various frequencies of the antenna elements of FIG. 6 on a user's wrist is illustrated. The Smith chart of FIG. 14 graphically illustrates circumferential frequency scaling and impedance matching. The Smith chart, as illustrated herein, shows an impedance matched circuit when the antenna elements of FIG. 6 are in the proximity of a user's wrist. As illustrated by FIG. 14, the antenna of FIG. 6 appears to provide good impedance matching when in contact with and/or in close proximity to the wrist of the user.

Figure 15:
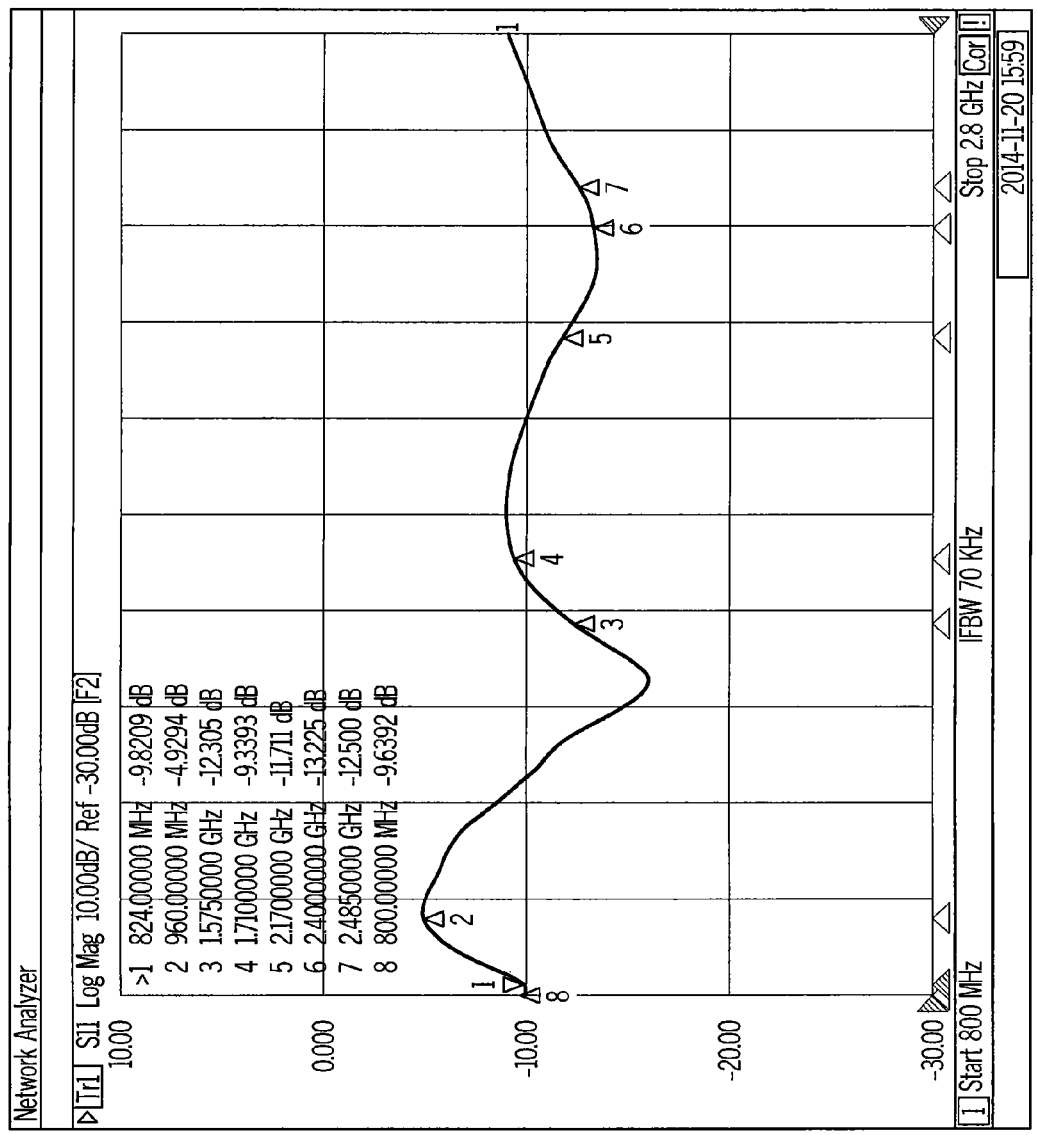
FIG. 15 illustrates the measured return loss at various frequencies when the wireless electronic device including the antenna elements of FIG. 6 is in contact with and/or in close proximity of a user's wrist.

Referring now to FIG. 15, the standing wave ratio for a wearable wireless electronic device including the antenna 300 of FIG. 6 when not in proximity of a user is illustrated. In other words, the wearable wireless electronic device 100 is not worn by the user in this case. The standing wave ratio of this antenna is very high (greater than a value of 10) over the entire frequency band. This graph appears to illustrate that the wearable wireless electronic device may not be used for communication at these frequencies when it is not worn by a user. As such, the wearable wireless electronic device 100 appears to show better performance when worn in contact with or in close proximity to the wrist of the user when compared to not being in close proximity to the user.

Figure 16:
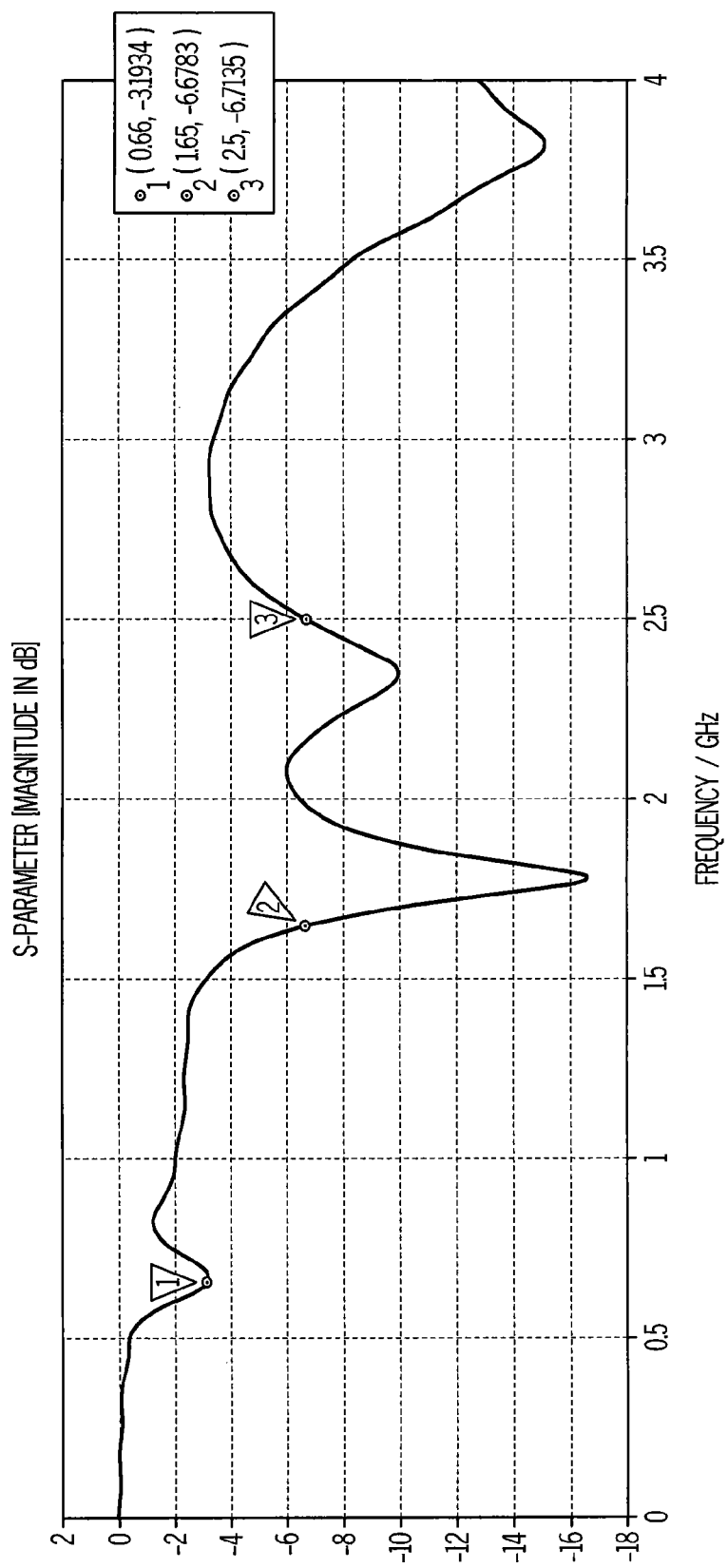
FIG. 16 illustrates the simulated return loss at various frequencies when the wireless electronic device including the antenna elements of FIG. 6 is in contact with and/or in close proximity of a user's wrist.

FIG. 16 illustrates the simulated return loss at various frequencies when the wireless electronic device 100 including the antenna elements of FIG. 6 is in contact with or in close proximity to a user's wrist. Good return loss may be shown as a loss value in dB in the range of −6 dB to −50 dB which indicates that the energy delivered by the device does not bounce back from the antenna, but rather is either absorbed or radiated. Absorption loss is when energy from the antenna is coupled into another element such as the body and absorbed rather than being radiated. For some antennas, such as monopole antennas, placing them near the user's body may improve return loss from about −6 dB to about −20 dB due to the added absorption loss. Mismatch loss may be the loss between the radio in the phone and the antenna, which may be caused by a poor return loss, such as close to 0 dB return loss.

Referring now to FIG. 16, the graph generally illustrates suitable return loss between about 1.65 and 2.5 GHz. Measurements indicate good impedance matching between 0.7 and 1 GHz, which is not illustrated by this simulation. The antenna of FIG. 6 may be suitable for use in communication across frequencies outlined in FIG. 9 as well as some frequencies not shown in this figure (for example, 2.2-2.4 GHz & higher frequencies). In other words, as illustrated by FIG. 16, the antenna of FIG. 6 provides suitable performance with suitable return losses when the first and second conductive antenna elements 600 and 607 are in contact with and/or in close proximity to the wrist of the user. The graph of FIG. 16 illustrates simulated return loss. In a measurement of the equivalent structure of FIG. 6, the return loss in the low-band may be significantly deeper and/or better since there may be some difficulties in recreating the properties of the human wrist in simulation.

Figure 17A:
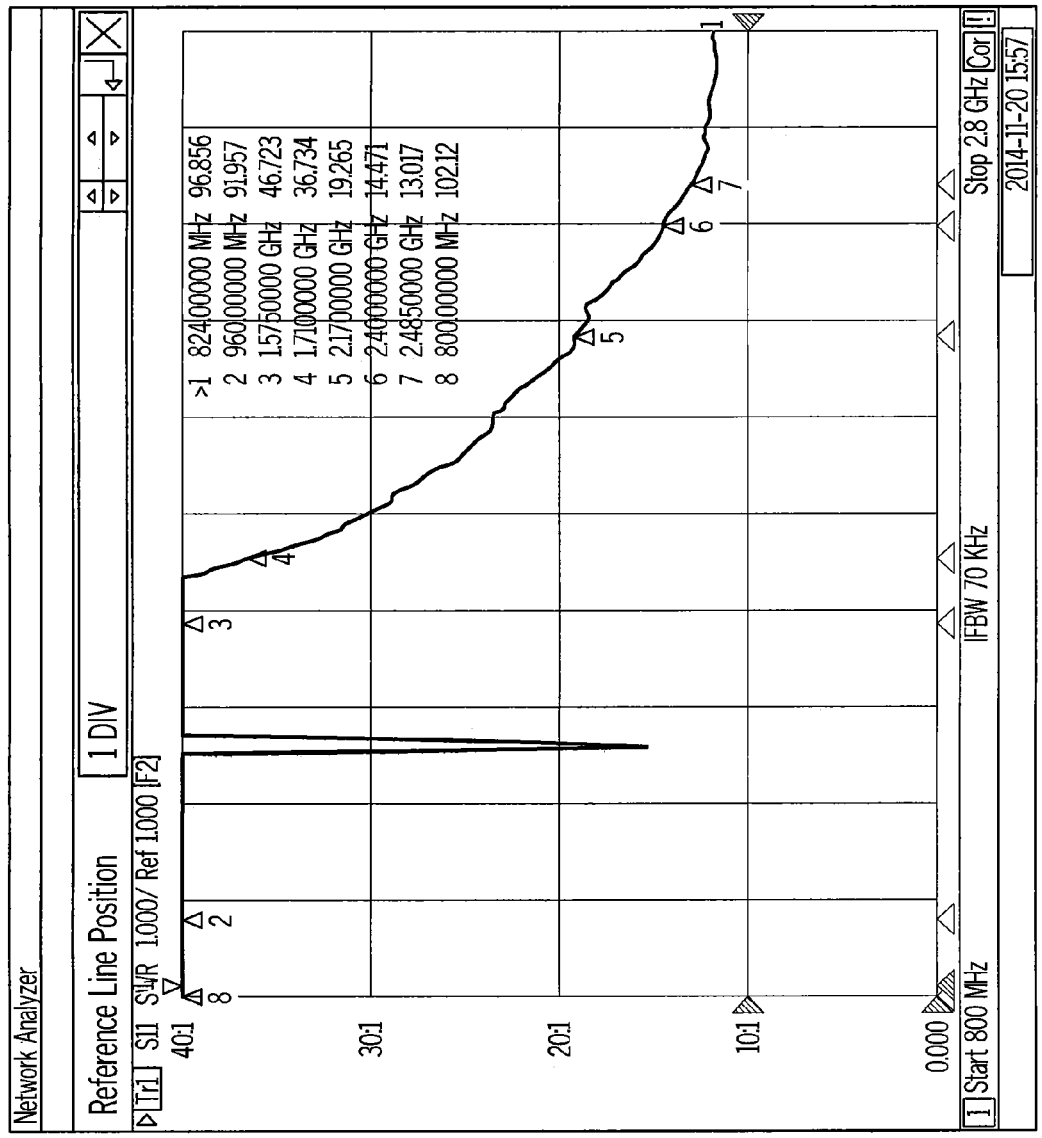
FIG. 17A illustrates the measured standing wave ratio at various frequencies when the wireless electronic device including the antenna elements of FIG. 6 are not near a user's wrist.

FIG. 17A illustrates the return loss at various frequencies when the wireless electronic device including the antenna elements of FIG. 6 are not in close proximity to a user's wrist. As seen from the graph, the return loss is fairly high across the entire illustrated frequency range of 800 MHz-2.8 GHz. As such, the antenna of FIG. 6 may not be suitable for use in communication in the illustrated frequency range.

Figure 17B:
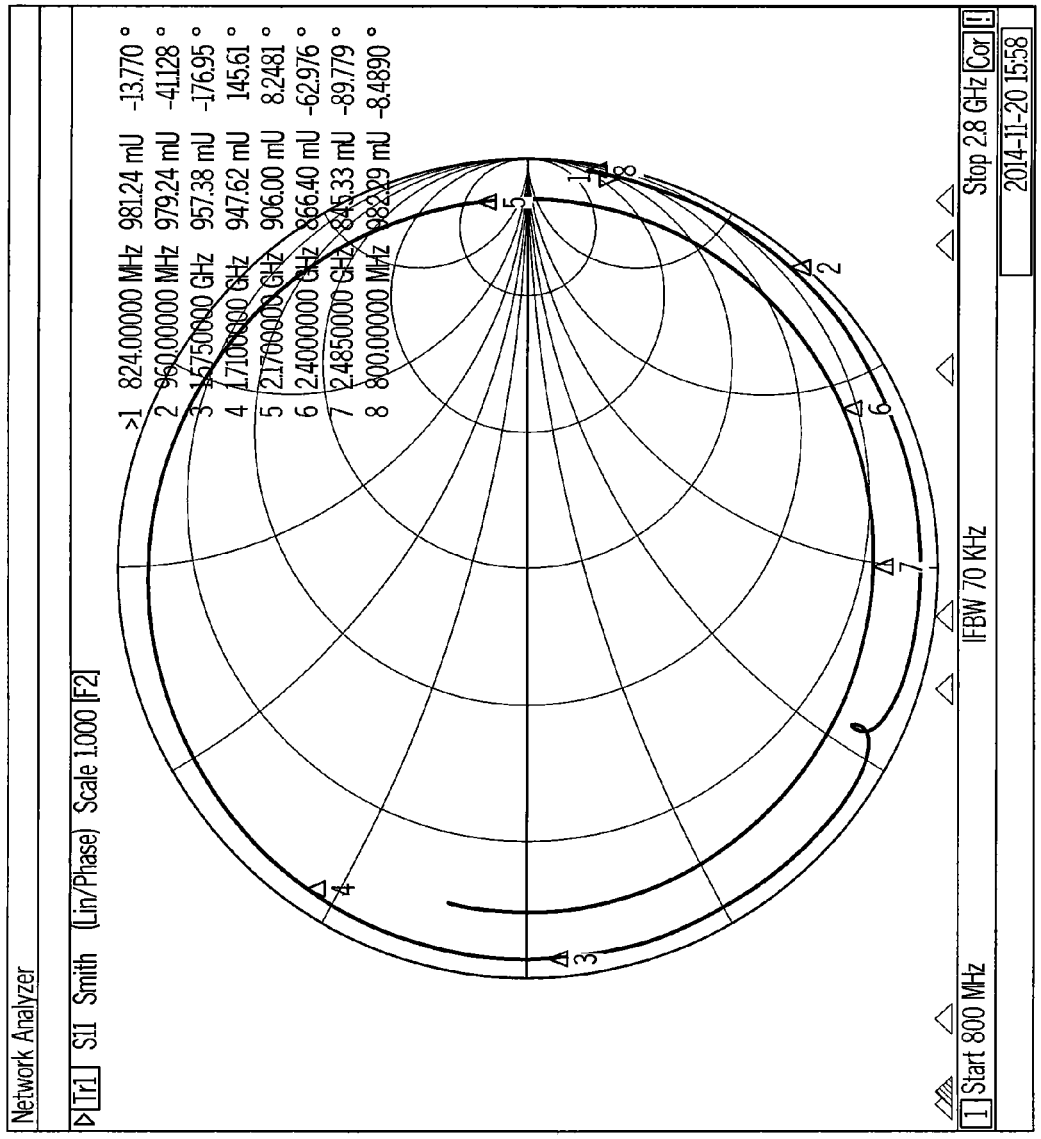
FIG. 17B illustrates a Smith chart at various frequencies when the wireless electronic device including the antenna elements of FIG. 6 are not near a user's wrist.

FIG. 17B illustrates a Smith chart at various frequencies when the wearable wireless electronic device 100 including the antenna elements of FIG. 6 are not in the proximity of a user's wrist. The Smith chart of FIG. 17B graphically illustrates circumferential frequency scaling and impedance matching. The Smith chart, as illustrated herein, shows a poorly impedance matched circuit when the antenna elements of FIG. 6 are not in the proximity of a user's wrist.

Figure 17C:
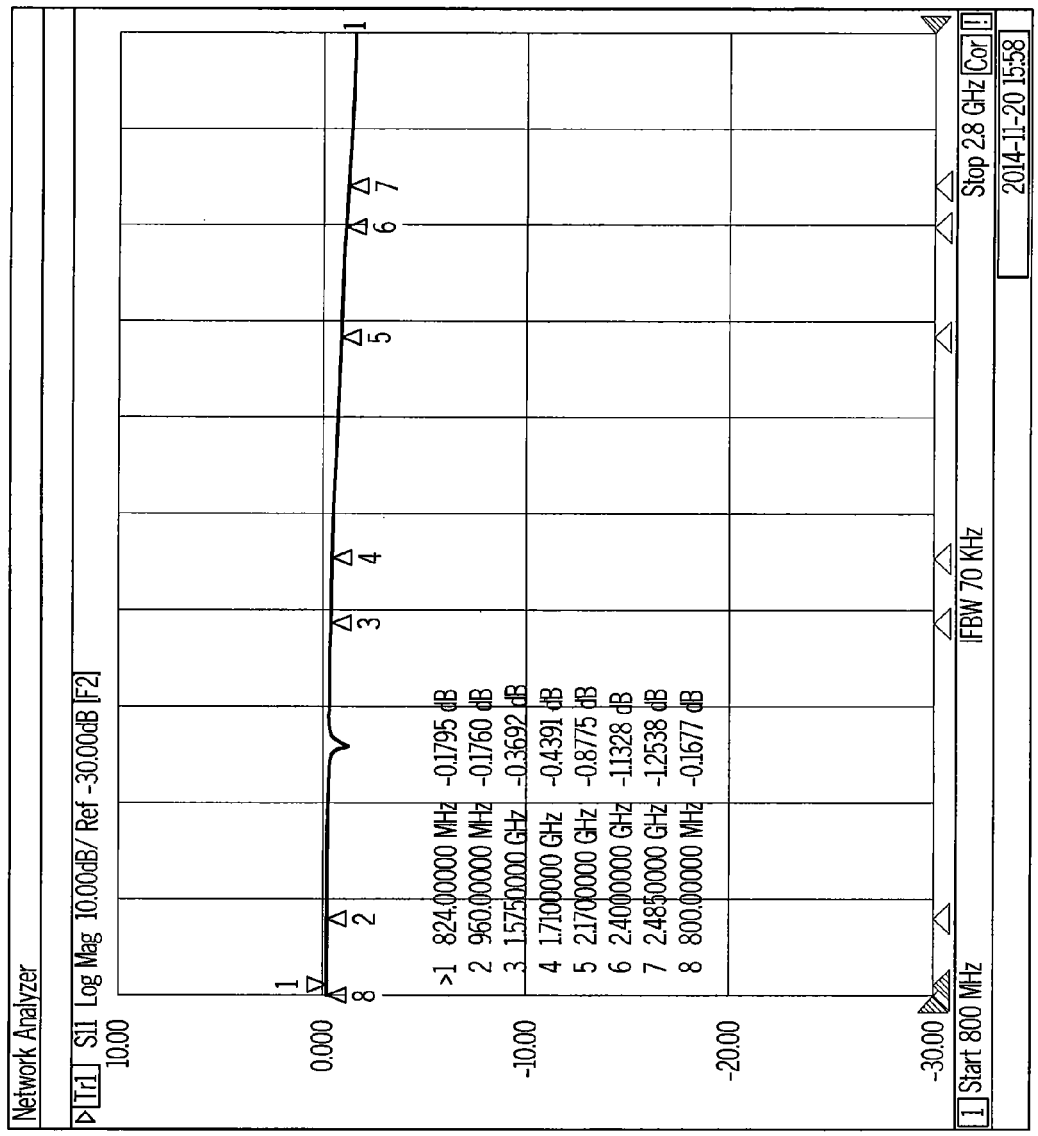
FIG. 17C illustrates the return loss at various frequencies when the wireless electronic device including the antenna elements of FIG. 6 are not near a user's wrist.

Referring now to FIG. 17C, the return loss at various frequencies when the wearable wireless electronic device 100 including the antenna elements of FIG. 6 is not in the proximity of a user's wrist is illustrated. The graph generally illustrates lower return losses (i.e. higher mismatch loss) when compared to the graph of FIG. 16. As such, the higher mismatch losses may be such that the wearable wireless electronic device 100 is not suitable for communication when the wearable wireless electronic device 100 is not in the proximity of the user's wrist.

Figure 18A:
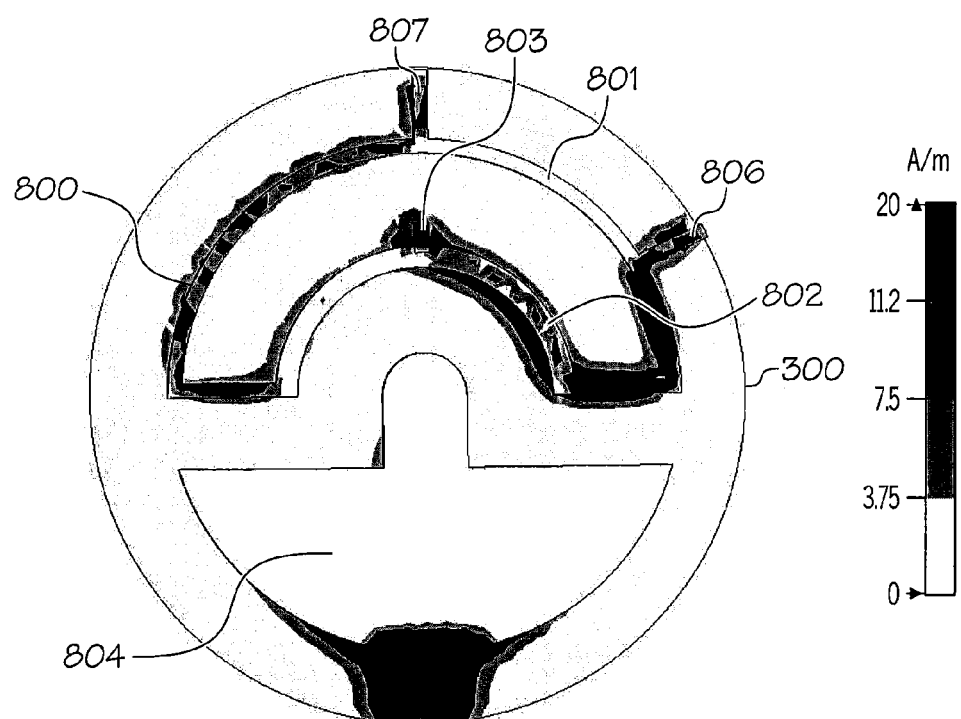
FIGS. 18A-21B illustrate the face current distribution and/or direction of current flow at various frequencies when the wearable wireless electronic device including the antenna elements of FIG. 8 is in contact with and/or in close proximity of a user's wrist.
Figure 18B:
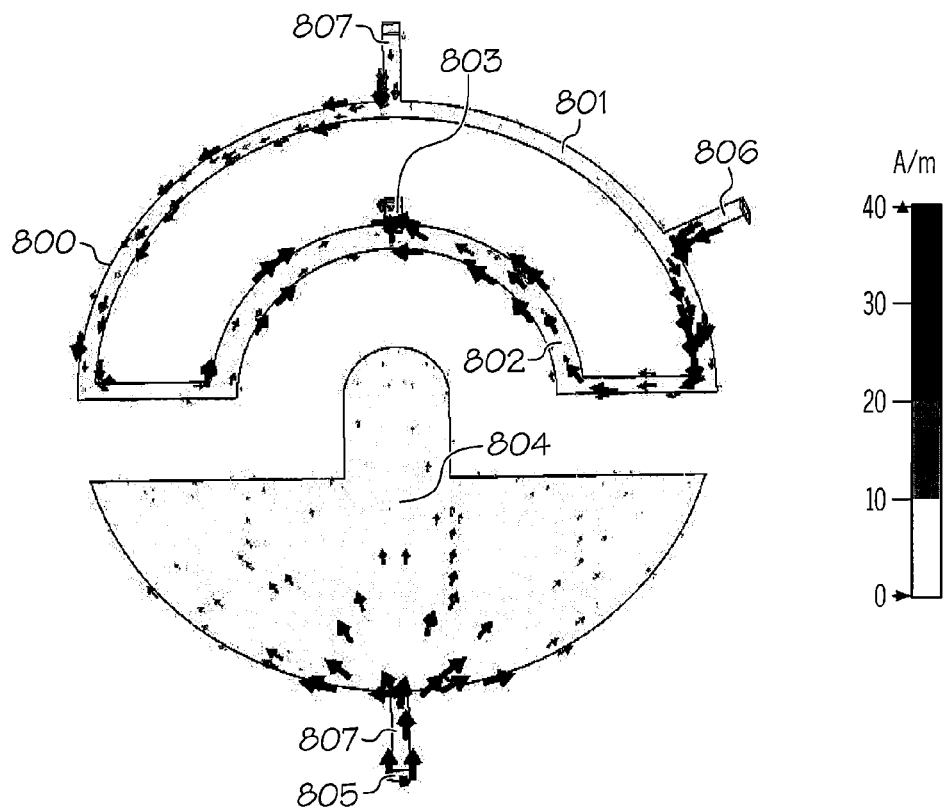

FIGS. 18A-21B illustrate the surface current distribution and direction of current flow at various frequencies when the wireless electronic device including the antenna elements of FIG. 8 is in contact with and/or in close proximity to a user's wrist. Although FIGS. 18A-21B are discussed in the context of the antenna of FIG. 8 as a non-limiting example, similar analysis and results may be obtained for any of the antennas of FIGS. 5-7. Referring now to FIG. 18A, the surface current distribution on the antenna 300 of FIG. 8 is illustrated when excited at 700 MHz. High levels of current may be present on portions of the first conductive antenna element 800, indicating that the antenna is resonant at this frequency. Current may be high at the feed via 803 and ground vias 806 and 807. Referring now to FIG. 18B, the direction of the current flow is represented by the arrows. For example, the current may flow between the feed via 803 and/or the ground via 807 of antenna element 800 through the ground plane of the printed circuit board 206 to the second conductive antenna element 804 through the ground via 805 and/or 807. The current direction of currents on the ground plane of the printed circuit board 206 and those of the ground extension of the second conductive antenna element 804 are opposite in direction. This may lead to a partial cancellation of fields radiated toward the user's wrist and/or arm, which may, in turn, lower the body loss for this structure relative to a monopole antenna and/or this configuration without second conductive antenna element 804. As such, the antenna of FIG. 8 provides suitable performance when in contact with and/or in close proximity to the wrist of the user.

Figure 19A:
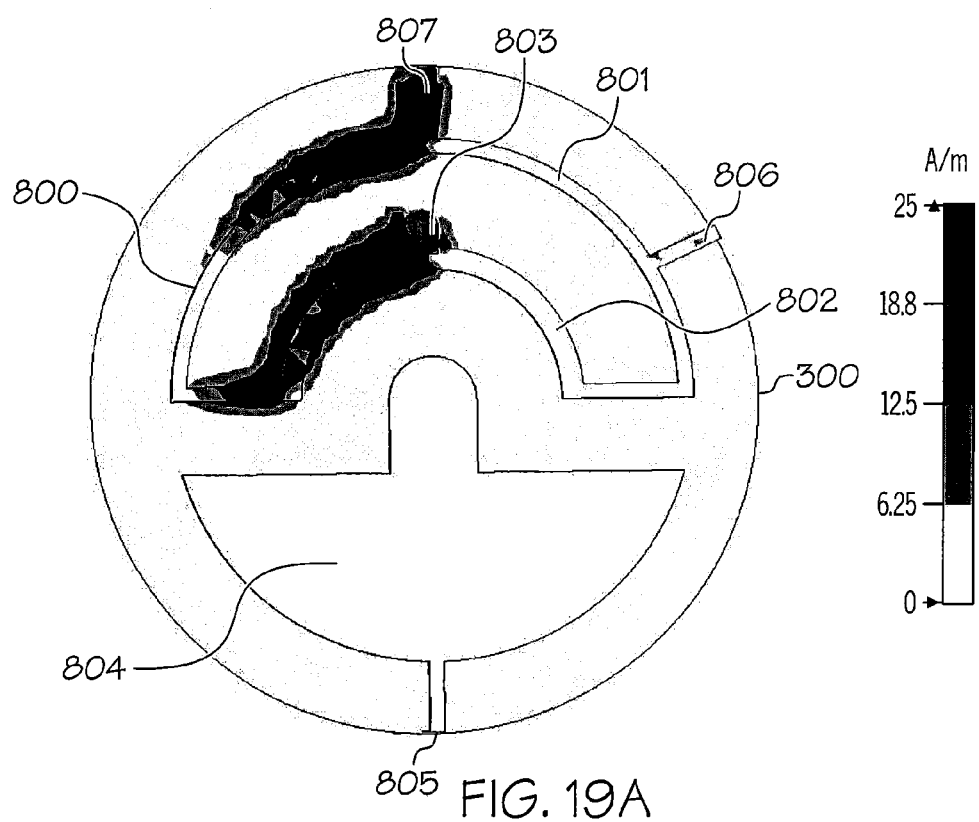
Figure 19B:
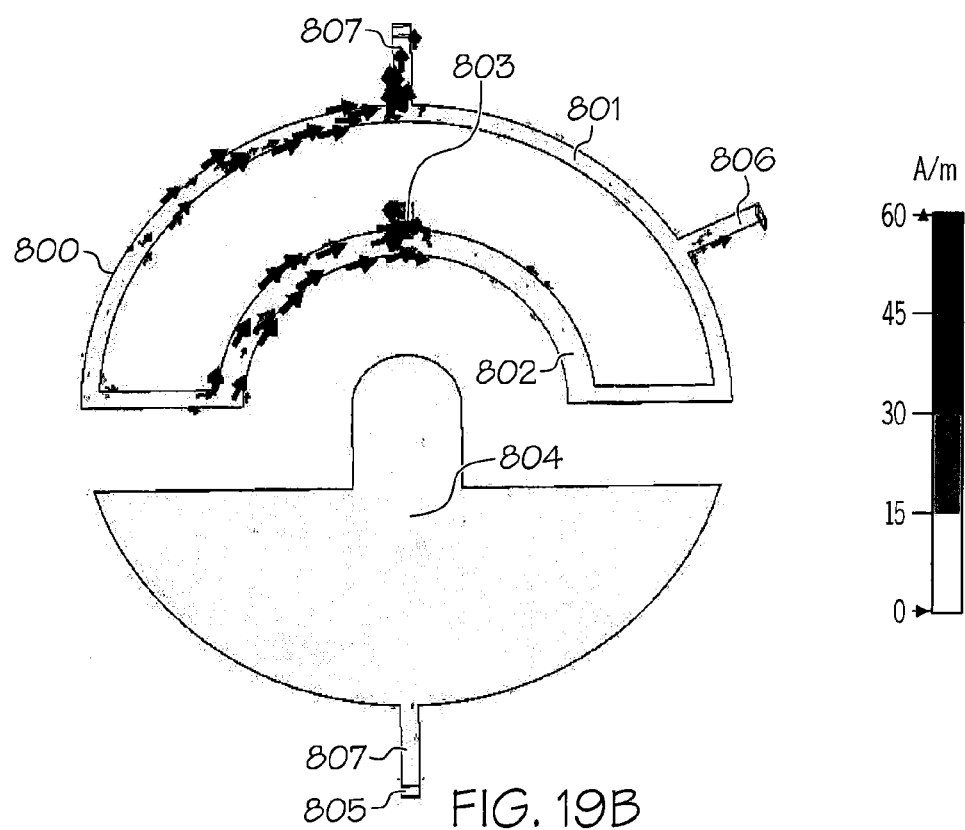

Referring now to FIG. 19A, the surface current distribution on the antenna 300 of FIG. 8 is illustrated when excited at 1500 MHz. High levels of current may be present on portions of the first conductive antenna element 800, indicating that the antenna is resonant at 1500 MHz. Current may be high at the feed via 803 and ground via 807. The ground plane extension of the second conductive antenna element 804 may be devoid of current indicating that it is not active at this frequency. Referring to FIG. 19B, the direction of current on the first conductive antenna element 800 may be towards the feed via 803 and the ground via 807 in respective branches of the first conductive antenna element 800. The path length between the feed via 803 and the ground via 807 may be approximately ½ wavelength in the loaded (i.e. body-worn) condition.

Figure 20A:
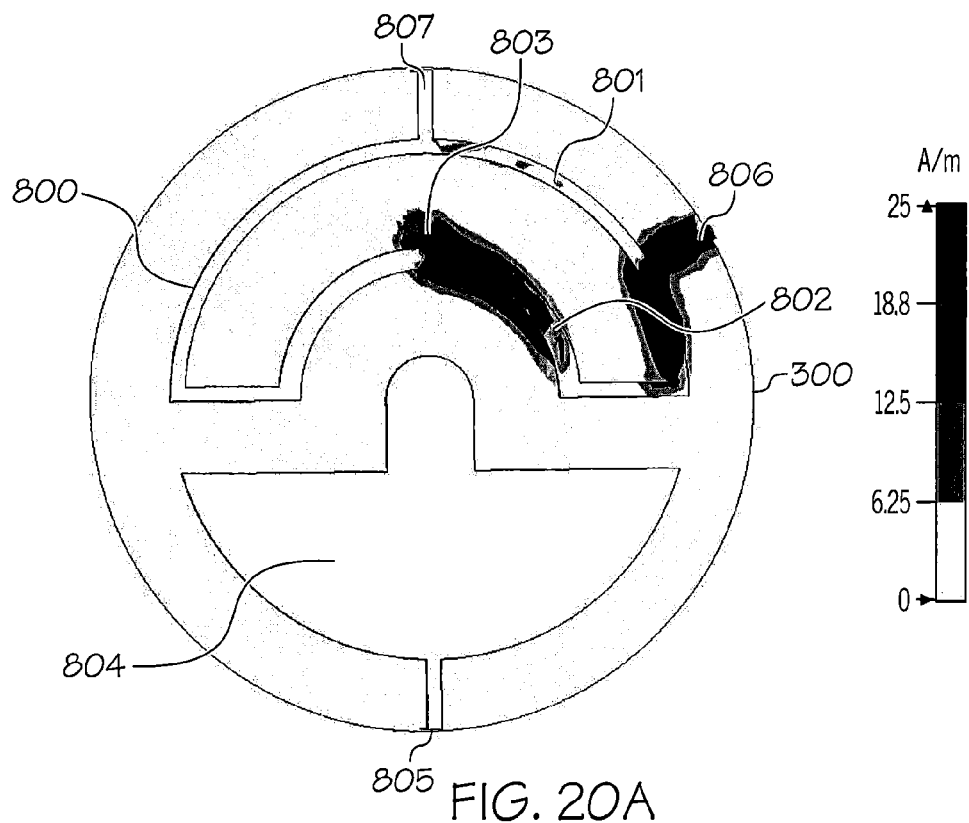
Figure 20B:
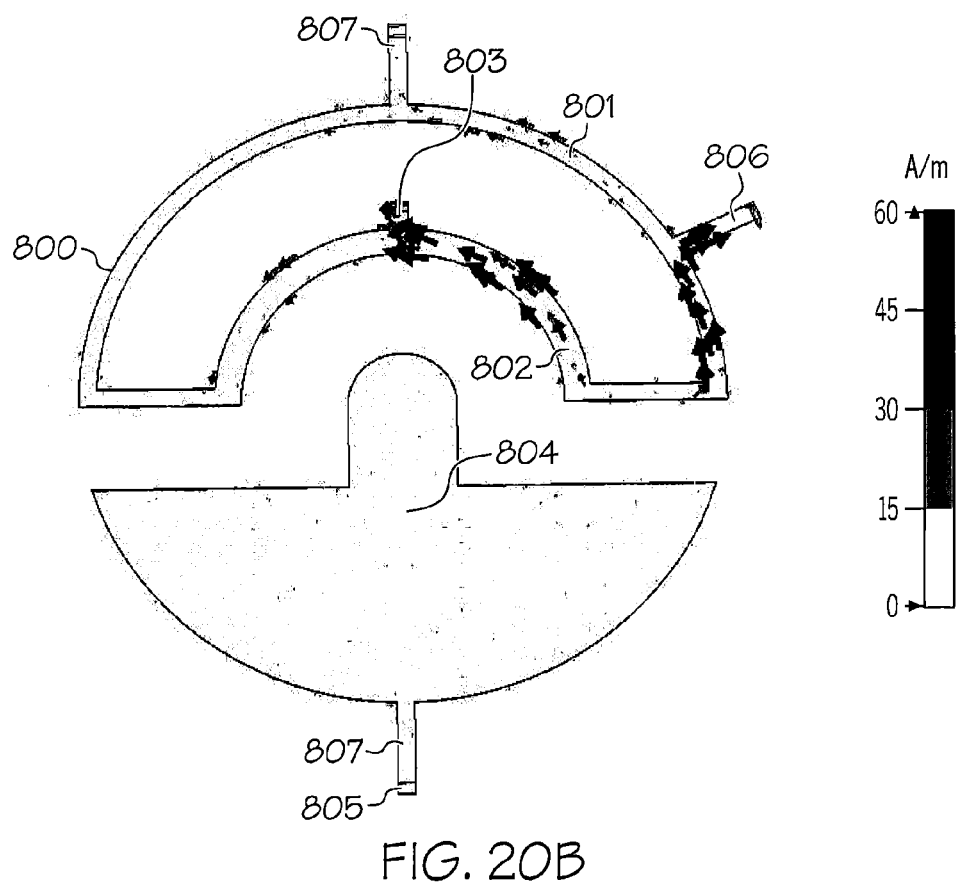

Referring now to FIG. 20A, the surface current distribution on the antenna 300 of FIG. 8 is illustrated when excited at 2000 MHz. High levels of current may be present on portions of the first conductive antenna element 800, indicating that the antenna is resonant at 2000 MHz. Current may be high at the feed via 803 and ground via 806. The structure may be essentially devoid of current on the ground plane extension of the second conductive antenna element 804 indicating that this part of the structure may not be particularly active at this frequency. Referring to FIG. 20B, the direction of current on the first conductive antenna element 800 may be towards the feed via 803 and the ground via 806 in respective branches of the first conductive antenna element 800. The current null between the high-current areas of the feed via 803 and the ground via 806 may indicate that the path length in the loaded test condition is approximately ½ wavelength at the test frequency of 2000 MHz.

Figure 21A:
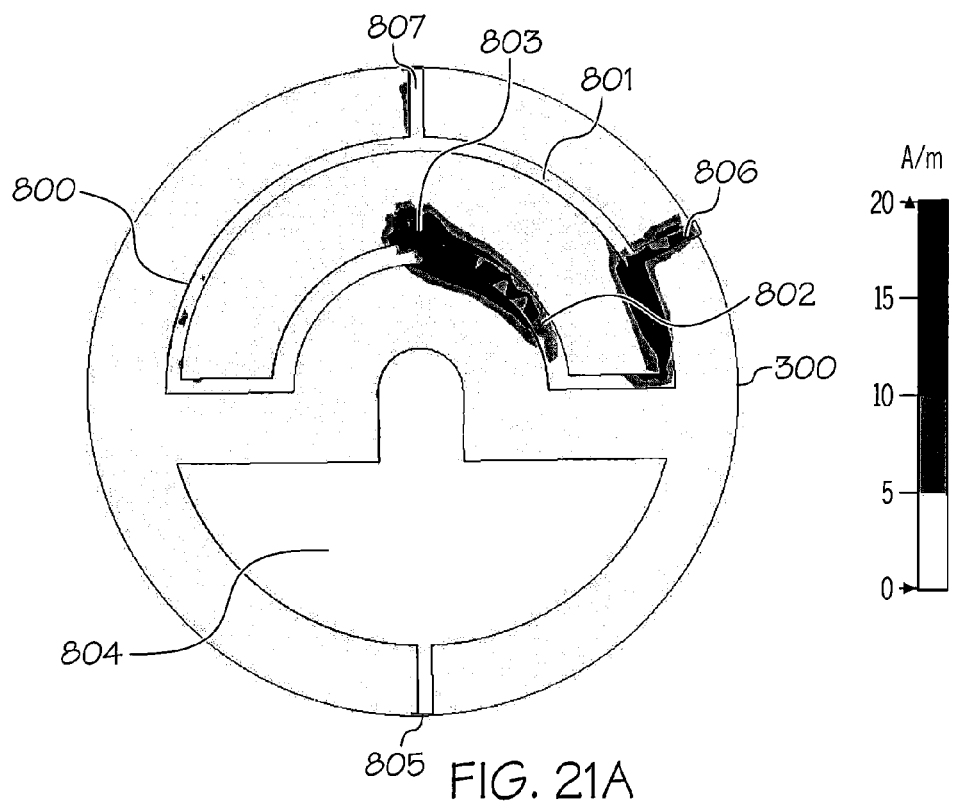
Figure 21B:
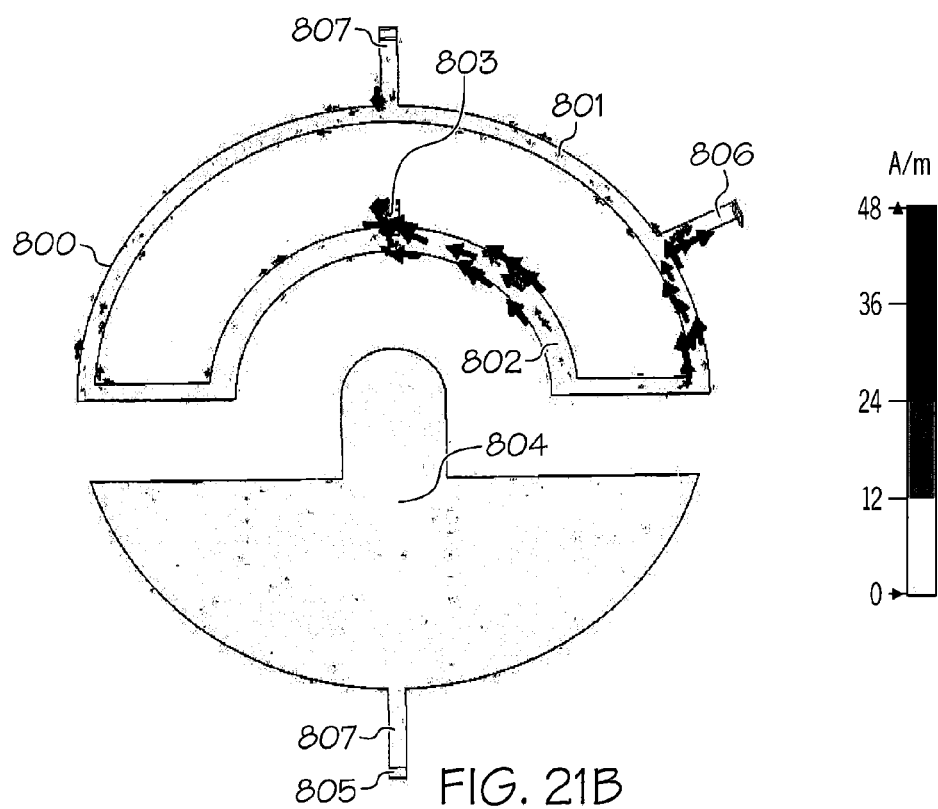

Referring now to FIG. 21A, the surface current distribution on the antenna 300 of FIG. 8 is illustrated when excited at 2300 MHz. High levels of current may be present on portions of the first conductive antenna element 800, indicating that the antenna is resonant at 2300 MHz. Current may be particularly high at the feed via 803 and ground via 806, similar to when excited at 2000 MHz, as illustrated in FIG. 20A. The structure may essentially be devoid of current on the ground plane extension of the second conductive antenna element 804 indicating that this part of the structure may not be particularly active at this frequency. Referring to FIG. 21B, the direction of current on the first conductive antenna element 800 may be towards the feed via 803 and the ground via 806 in respective branches of the first conductive antenna element 800. The current null between the high-current areas of the feed via 803 and the ground via 806 may indicate that the path length in the loaded test condition is approximately ½ wavelength at the test frequency of 2300 MHz.

According to some embodiments described here, as illustrated by the measurements and/or simulations of FIGS. 9-21B, the lowband frequencies may not be suitable for communication with a 3 mm separation from the wrist of the user since 10 dB to 15 dB of efficiency reduction may be exhibited. The highband frequencies do not appear to rely on the user's body to radiate to the same extent, since the performance degradation appears to be less than the lowband degradation. With small separations such as <3 mm, a frequency shift may be exhibited. At lowband frequencies, the performance seems to drop more rapidly when compared to highband frequencies. The user's body may provide matching for the antenna and may function similar to a ground plane by allowing the wearable wireless electronic device to radiate. Without the user's body, the capacitance between the antenna element and the ground plane may be too high and currents may not be excited on the antenna. The wearable wireless electronic device may provide the bulk of the far-field radiation. At lower frequencies, the user's body may be more conductive. At higher frequencies, the user's body may be more lossy. Hence, the lowband and highband frequencies for the antenna structures described herein may not use the same mechanisms to achieve performance. The ground plane extension appears to be active and/or relevant in the lowband frequency ranges.

The above discussed antenna structures for wearable wireless electronic devices include conductive antenna elements that may be in contact with and/or in close proximity to the user. The antennas of FIGS. 3-8 may use the wrist of the user for impedance matching the antenna. These antennas may be poorly impedance matched when not in the proximity of the user and thus may not be suitable for communication when not in the proximity of the user. Some embodiments of the antennas described herein may be suitable for lowband frequency applications such as LTE and/or GSM in the range between 700 MHz-1000 MHz. Some embodiments described herein may be well suited for applications such as GPS and/or UMTS in the 1500 MHz-2200 MHz frequency range. Antennas in some embodiments appear to be suitable for applications such as Bluetooth and/or Wi-Fi in the 2.4 GHz-2.5 GHz range. The antennas of FIGS. 5-8 may resonate at multiple frequency bands and thus may be used for a variety of applications in the aforementioned frequency ranges.

As described herein, the antenna matching may be degraded when removed from close proximity to the user's wrist. However, a desk-stand and/or a charger may be utilized that assists in impedance matching the antenna when the device is not in close proximity to the wrist of the user. The desk-stand and/or charger may include an extension comprising metal components that extend perpendicularly from the face 201*b* of FIG. 2 of the wearable wireless electronic device 100. This extension may be configured to restore the antenna resonance frequencies, impedance matching, and/or performance. As a non-limiting example, the extension may be about 20 mm in length.

Many different embodiments have been disclosed herein, in connection with the above description and the drawings. It will be understood that it would be unduly repetitious and obfuscating to literally describe and illustrate every combination and subcombination of these embodiments. Accordingly, the present specification, including the drawings, shall be construed to constitute a complete written description of all combinations and subcombinations of the embodiments described herein, and of the manner and process of making and using them, and shall support claims to any such combination or subcombination.

In the drawings and specification, there have been disclosed various embodiments and, although specific terms are employed, they are used in a generic and descriptive sense only and not for purposes of limitation.

What is claimed is:

1. A wearable wireless electronic device, the wearable wireless electronic device comprising:
a first conductive antenna element of an antenna that is electrically coupled to an antenna feed of the antenna; and
a second conductive antenna element of the antenna that is electrically coupled to a ground plane of the antenna, wherein the first conductive antenna element and the second conductive antenna element are configured to be in direct contact with a body of a user when the wearable wireless electronic device is worn by the user.

2. The wearable wireless electronic device of claim 1, wherein the first and second conductive antenna elements are configured to provide capacitive coupling between the body of the user and the antenna such that the antenna resonates at one or more resonant frequencies when coupled to the body of the user.

3. The wearable wireless electronic device of claim 2, wherein the capacitive coupling between the body of the user and the antenna provides impedance matching to the antenna to reduce return loss of the antenna when coupled to the body of the user.

4. The wearable wireless electronic device of claim 3, wherein the first and second conductive antenna elements are configured to reduce the impedance matching of the antenna when the wearable wireless electronic device is removed from the direct contact with the body of the user.

5. The wearable wireless electronic device of claim 3, wherein the first and second conductive antenna elements are configured to prevent the antenna from resonating at the one or more resonant frequencies when the wearable wireless electronic device is removed from the direct contact with the body of the user.

6. The wearable wireless electronic device of claim 1, wherein the first and second conductive antenna elements are configured to reduce impedance matching of the antenna when the wearable wireless electronic device is removed from the direct contact with the body of the user.

7. The wearable wireless electronic device of claim 2, wherein the first and second conductive antenna elements are configured to prevent the antenna from resonating at the one or more resonant frequencies when the wearable wireless electronic device is removed from the direct contact with the body of the user.

8. The wearable wireless electronic device of claim 2, wherein the one or more resonant frequencies comprises a lowband resonant frequency and a highband resonant frequency that is higher than the lowband resonant frequency.

9. The wearable wireless electronic device of claim 8, wherein the lowband resonant frequency comprises frequencies between 700 MHz and 1000 MHz.

10. The wearable wireless electronic device of claim 9, wherein the highband resonant frequency comprises frequencies between 1.5 GHz and 2.5 GHz.

11. The wearable wireless electronic device of claim 1, further comprising:
a case comprising a first face and a second face that is remote the first face, wherein the second face is configured to be adjacent the body of the user; and
a plurality of microelectronic devices in the case,
wherein the first and second conductive antenna elements are outside the case, protruding from the second face of the case toward the body of the user.

12. The wearable wireless electronic device of claim 11, wherein the second conductive antenna element extends from a coupling via along the second face of the case, away from an edge of the case, and
wherein the coupling via is located near the edge of the case and electrically couples the second conductive antenna element to the ground plane of the antenna.

13. The wearable wireless electronic device of claim 12, wherein the second conductive antenna element comprises a fork-shaped structure that extends along the second face of the case.

14. The wearable wireless electronic device of claim 12, wherein the second conductive antenna element comprises one or more hollow half moon-shaped structures that extend along the second face of the case.

15. The wearable wireless electronic device of claim 12, wherein the second conductive antenna element comprises one or more filled half moon-shaped structures that extend along the second face of the case.

16. The wearable wireless electronic device of claim 11, wherein the first conductive antenna element comprises at least one approximately circular shape along an edge of the case that extends along the second face of the case.

17. The wearable wireless electronic device of claim 16, wherein the at least one approximately circular shape comprises two approximately concentric partial circular shapes.

18. The wearable wireless electronic device of claim 17, wherein one of the two approximately concentric partial circular shapes comprises an omega shaped structure.

19. The wearable wireless electronic device of claim 1, wherein the first conductive antenna element is electrically coupled to the antenna feed through a feed via.

20. The wearable wireless electronic device of claim 19, wherein the first conductive antenna element is electrically coupled to the ground plane of the antenna through a one or more ground vias.

21. A wearable wireless electronic device, the wearable wireless electronic device comprising:
an antenna comprising a conductive antenna element that is electrically coupled to an antenna feed,
wherein the conductive antenna element is configured to provide capacitive coupling between a body of a user and the antenna such that the antenna resonates at a resonant frequency when the wearable wireless electronic device is worn by the user such that the conductive antenna element is in direct contact with the body of the user, and
wherein the capacitive coupling between the user and the antenna provides impedance matching to the antenna that comprises the conductive antenna element and the antenna feed.

22. The wearable wireless electronic device of claim 21, wherein the impedance matching provided by the capacitive coupling between the user and the antenna reduces return loss of the antenna.

23. The wearable wireless electronic device of claim 21, wherein the wearable wireless electronic device is configured to be worn on the wrist of the user.

24. The wearable wireless electronic device of claim 21, wherein the conductive antenna element is configured to reduce the impedance matching of the antenna when the wearable wireless electronic device is removed from the direct contact with the body of the user.

25. The wearable wireless electronic device of claim 21, wherein the conductive antenna element is configured to prevent the antenna from resonating at the resonant frequency when the wearable wireless electronic device is removed from the direct contact with the body of the user.

26. A wearable wireless electronic device, the wearable wireless electronic device comprising:
a case comprising a first face and a second face that opposes the first face, wherein the first and second faces define a periphery of the wearable wireless electronic device;
a plurality of microelectronic devices in the case;
a first antenna element on the first face of the case and outside the case, the first antenna element conforming to a portion of a periphery of the case;
a second antenna element on the first face. of the case and outside the case that extends from an edge of the first face of the case towards the center of the first face of the case;
a feed via that extends from the first face of the case into the case and electrically connects the first antenna element to an antenna feed inside the case; and
a ground via that extends from the first face of the case into the case and electrically connects the second antenna element to a ground plane inside the case.

27. The wearable wireless electronic device of claim 1, wherein the wearable wireless electronic device is configured to be worn on a wrist of the user.

* * * * *

UNITED STATES PATENT AND TRADEMARK OFFICE
CERTIFICATE OF CORRECTION

PATENT NO. : 9,653,785 B2  
APPLICATION NO. : 14/603438  
DATED : May 16, 2017  
INVENTOR(S) : Vance Page 1 of 1

It is certified that error appears in the above-identified patent and that said Letters Patent is hereby corrected as shown below:

In the Claims

Column 18, Claim 22, Line 3: Please correct "between the user and"
to read -- between the body of the user and --
Claim 26, Line 30: Please correct "the first face. of"
to read -- the first face of --

Signed and Sealed this
Twenty-seventh Day of March, 2018

Andrei Iancu
*Director of the United States Patent and Trademark Office*